US007297478B1

(12) United States Patent
Reinl et al.

(10) Patent No.: US 7,297,478 B1
(45) Date of Patent: *Nov. 20, 2007

(54) CREATION OF VARIABLE LENGTH AND SEQUENCE LINKER REGIONS FOR DUAL-DOMAIN OR MULTI-DOMAIN MOLECULES

(75) Inventors: Stephen J. Reinl, Sacramento, CA (US); John A. Lindbo, Vacaville, CA (US); Thomas Turpen, Vacaville, CA (US)

(73) Assignee: Large Scale Biology Corporation, Vacaville, CA (US)

( * ) Notice: Subject to any disclaimer, the term of this patent is extended or adjusted under 35 U.S.C. 154(b) by 402 days.

This patent is subject to a terminal disclaimer.

(21) Appl. No.: 09/667,237

(22) Filed: Sep. 22, 2000

(51) Int. Cl.
*C12Q 1/68* (2006.01)
*C07H 21/04* (2006.01)

(52) U.S. Cl. ............ 435/6; 435/DIG. 37; 435/DIG. 47; 536/24.2

(58) Field of Classification Search .................... 435/6, 435/DIG. 37, DIG. 47; 536/24.2
See application file for complete search history.

(56) References Cited

U.S. PATENT DOCUMENTS

| | | | |
|---|---|---|---|
| 4,816,567 A | 3/1989 | Cabilly et al. | |
| 5,013,653 A | 5/1991 | Huston et al. | |
| 5,260,203 A | 11/1993 | Ladner et al. | |
| 5,443,953 A | 8/1995 | Hansen et al. | |
| 5,585,089 A | 12/1996 | Queen et al. | |
| 5,624,821 A | 4/1997 | Winter et al. | |
| 5,747,334 A | 5/1998 | Kay et al. | |
| 5,837,242 A * | 11/1998 | Holliger et al. | 424/136.1 |
| 6,040,431 A * | 3/2000 | Keck et al. | 530/399 |
| 6,403,371 B1 | 6/2002 | Conrad et al. | |

FOREIGN PATENT DOCUMENTS

| | | |
|---|---|---|
| EP | 0349578 | 3/1988 |
| WO | 90/05144 | 5/1990 |
| WO | WO 91/19818 | * 12/1991 |
| WO | 92/01047 | 1/1992 |
| WO | 9412520 | 6/1994 |
| WO | 9612028 | 4/1996 |
| WO | 9902710 | 1/1999 |
| WO | 00/43507 | 7/2000 |

OTHER PUBLICATIONS

Cwirla et al., Proc. Natl. Acad. Sci. USA, vol. 87, pp. 6378-6382, Aug. 1990.*
Shu, et al., "Secretion of a single-gene-encoded immunoglobulin from myeloma cells", *Proc. Natl. Acad. Sci. USA* (1993) 90:7995-7999.
Vaquero, et al., "Transient expression of a tumor-specific single-chain fragment and a chimeric antibody in tobacco leaves", *Proc.. Natl. Acad Sci.* (1999), 96:11128-11133.
Langeveld et al., Effective induction of neutralizing antibodies with the amino terminus of VP2 of canine parvovirus as a synthetic peptide, Vaccine, 1994, vol. 12, pp. 1473-1480.
Fitchen et al., Plant virus espressing hybrid coat protein with added murine epitope elicits autoantibody response, Vaccine, 1995, vol. 13, pp. 1051-1057.
Jerala et al., Improved Expression and Evaluation of Polyethyleneimine Precipitation in Isolation of Recombinant Cysteine Proteinase Inhibitor Stefin B, Protein Expression and Purification, 1994, pp. 65-69.
*Protein Engineering*, vol. 11, No. 5, pp, 405-410, (1998). Hennecke F. et al., "Non-repetative single-chain Fv linker selected by selectively infective phage (SIP) technology."
Tang, Ying et al., "Selection of Linkers for a Catalytic Single-Chain Antibody Using Phage Display Technology", *J. Biol. Chem.*, vol. 271, No. 26, 1996, pp. 15682-15686.
Turner, D.J. et al., "Importance of the Linker in Expression of Single-Chain Fv Antibody Fragments: Optimisation of Peptide Sequence Using Phage Display Technology", *J. Immunol.* Methods, vol. 205, 1997, pp. 43-54.
Simoncsits, András et al., "Isolation of Altered Specificity Mutants of the Single-Chain 434 Repressor That Recognize Asymmetric DNA Sequences Containing the TTA and TTAC Subsites", *Nucl. Acids Res.*, vol. 27, No. 17, Sep. 1999 (1999-09), pp. 3474-3480.

* cited by examiner

*Primary Examiner*—Mark L. Shibuya
(74) *Attorney, Agent, or Firm*—Wayne P. Fitzmaurice; R. Thomas Gallegos

(57) ABSTRACT

Disclosed are methods and compositions for creating a DNA, RNA or protein molecule with two or more nucleic acid or polypeptide domains, respectively, joined by a linker region. These methods are used to generate random linker libraries of nucleic acids that encode dual-domain or multi-domain polypeptides. The linker regions are characterized by both length and sequence variability.

2 Claims, 3 Drawing Sheets

SEQUENCE LISTING

```
<160> NUMBER OF SEQ ID NOS: 52

<210> SEQ ID NO 1
<211> LENGTH: 9
<212> TYPE: PRT
<213> ORGANISM: Artificial
<220> FEATURE:
<223> OTHER INFORMATION: Glycine rich linker

<400> SEQUENCE: 1

Pro Gly Ile Ser Gly Gly Gly Gly Gly
1               5

<210> SEQ ID NO 2
<211> LENGTH: 16
<212> TYPE: PRT
<213> ORGANISM: Artificial
<220> FEATURE:
<223> OTHER INFORMATION: Asparagine rich linker

<400> SEQUENCE: 2

Asn Asn Asn Asn Asn Asn Asn Asn Asn Asn Leu Gly Ile Glu Gly Arg
1               5                   10                  15

<210> SEQ ID NO 3
<211> LENGTH: 15
<212> TYPE: PRT
<213> ORGANISM: Artificial
<220> FEATURE:
<223> OTHER INFORMATION: (Gly4-Ser)3

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 30
<212> TYPE: DNA
<213> ORGANISM: Artificial
<220> FEATURE:
<223> OTHER INFORMATION: VH domain forward primer, chemically
      synthesized
```

-continued

```
<400> SEQUENCE: 4
gtggcatgca ggttcaactg gtggagtctg                                      30

<210> SEQ ID NO 5
<211> LENGTH: 26
<212> TYPE: DNA
<213> ORGANISM: Artificial
<220> FEATURE:
<223> OTHER INFORMATION: VH domain reverse primer, chemically
      synthesized
<220> FEATURE:
<221> NAME/KEY: misc_feature
<222> LOCATION: (1)..(3)
<223> OTHER INFORMATION: "asy" can appear from 1 to 50 times before the
      remainder of the sequence

<400> SEQUENCE: 5
asytgaggag acggtgacca gggttc                                          26

<210> SEQ ID NO 6
<211> LENGTH: 41
<212> TYPE: DNA
<213> ORGANISM: Artificial
<220> FEATURE:
<223> OTHER INFORMATION: VH domain reverse primer, first reaction,
      chemically synthesized

<400> SEQUENCE: 6
asyasyasya syasyasytg aggagacggt gaccagggtt c                         41

<210> SEQ ID NO 7
<211> LENGTH: 50
<212> TYPE: DNA
<213> ORGANISM: Artificial
<220> FEATURE:
<223> OTHER INFORMATION: VH domain reverse primer, second reaction,
      chemically synthesized

<400> SEQUENCE: 7
asyasyasya syasyasyas yasyasytga ggagacggtg accagggttc                50

<210> SEQ ID NO 8
<211> LENGTH: 29
<212> TYPE: DNA
<213> ORGANISM: Artificial
<220> FEATURE:
<223> OTHER INFORMATION: VL domain forward primer, chemically
      synthesized
<220> FEATURE:
<221> NAME/KEY: misc_feature
<223> OTHER INFORMATION: "rst" can appear from 1 to 50 times before the
      remainder of the sequence
<220> FEATURE:
<221> NAME/KEY: misc_feature
<222> LOCATION: (1)..(3)
<223> OTHER INFORMATION: "rst" can appear from 1 to 50 times before the
      remainder of the sequence

<400> SEQUENCE: 8
rstgacattc agatgaccca gtctccttc                                       29

<210> SEQ ID NO 9
<211> LENGTH: 39
<212> TYPE: DNA
<213> ORGANISM: Artificial
<220> FEATURE:
<223> OTHER INFORMATION: VL domain reverse primer, chemically
      synthesized
```

```
<400> SEQUENCE: 9 cacccctaggc tatcgtttga tcagtaccct ggtccccctg                          39

<210> SEQ ID NO 10
<211> LENGTH: 44
<212> TYPE: DNA
<213> ORGANISM: Artificial
<220> FEATURE:
<223> OTHER INFORMATION: VL domain forward primer, third reaction,
      chemically synthesized

<400> SEQUENCE: 10
rstrstrstr strstrstga cattcagatg acccagtctc cttc                     44

<210> SEQ ID NO 11
<211> LENGTH: 53
<212> TYPE: DNA
<213> ORGANISM: Artificial
<220> FEATURE:
<223> OTHER INFORMATION: VL domain forward primer, fourth reaction,
      chemically synthesized

<400> SEQUENCE: 11
rstrstrstr strstrstrs trstrstgac attcagatga cccagtctcc ttc           53

<210> SEQ ID NO 12
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 12
actactgcta ctggtgctag tactactgct ggtgctagt                            39

<210> SEQ ID NO 13
<211> LENGTH: 13
<212> TYPE: PRT
<213> ORGANISM: Artificial
<220> FEATURE:
<223> OTHER INFORMATION: Linker region amino acid sequence

<400> SEQUENCE: 13

Thr Thr Ala Thr Gly Ala Ser Thr Thr Ala Gly Ala Ser
1               5                   10

<210> SEQ ID NO 14
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 14
gctactgctg ctagtggtgc tgctgctggt ggtggtact                            39

<210> SEQ ID NO 15
<211> LENGTH: 13
<212> TYPE: PRT
<213> ORGANISM: Artificial
<220> FEATURE:
<223> OTHER INFORMATION: Linker region amino acid sequence
```

```
<400> SEQUENCE: 15

Ala Thr Ala Ala Ser Gly Ala Ala Ala Gly Gly Gly Thr
1               5                   10

<210> SEQ ID NO 16
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 16
gctactggtg ctagtactag tgctactgct ggtggtagt                              39

<210> SEQ ID NO 17
<211> LENGTH: 13
<212> TYPE: PRT
<213> ORGANISM: Artificial
<220> FEATURE:
<223> OTHER INFORMATION: Linker region amino acid sequence

<400> SEQUENCE: 17

Ala Thr Gly Ala Ser Thr Ser Ala Thr Ala Gly Gly Ser
1               5                   10

<210> SEQ ID NO 18
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 18
agtactgctg ctggtactag tagtggtagt agtactggt                              39

<210> SEQ ID NO 19
<211> LENGTH: 13
<212> TYPE: PRT
<213> ORGANISM: Artificial
<220> FEATURE:
<223> OTHER INFORMATION: Linker region amino acid sequence

<400> SEQUENCE: 19

Ser Thr Ala Ala Gly Thr Ser Ser Gly Ser Ser Thr Gly
1               5                   10

<210> SEQ ID NO 20
<211> LENGTH: 51
<212> TYPE: DNA
<213> ORGANISM: Artificial
<220> FEATURE:
<223> OTHER INFORMATION: Linker region nucleotide sequence, chemically
      synthesized

<400> SEQUENCE: 20
gctagtactg ctactagtag tggtggtggt ggtactggta gtagtgctgc t                51

<210> SEQ ID NO 21
<211> LENGTH: 17
<212> TYPE: PRT
<213> ORGANISM: Artificial
<220> FEATURE:
<223> OTHER INFORMATION: Linker region amino acid sequence
```

```
<400> SEQUENCE: 21

Ala Ser Thr Ala Thr Ser Ser Gly Gly Gly Thr Gly Ser Ser Ala Ala
1               5                   10                  15

Ala

<210> SEQ ID NO 22
<211> LENGTH: 60
<212> TYPE: DNA
<213> ORGANISM: Artificial
<220> FEATURE:
<223> OTHER INFORMATION: Linker region nucleotide sequence, chemically
      synthesized

<400> SEQUENCE: 22
gctactagta ctgctgctgc tggtgctact agtgctactg gtggtgctag tggtactggt      60

<210> SEQ ID NO 23
<211> LENGTH: 20
<212> TYPE: PRT
<213> ORGANISM: Artificial
<220> FEATURE:
<223> OTHER INFORMATION: Linker region amino acid sequence

<400> SEQUENCE: 23

Ala Thr Ser Thr Ala Ala Ala Gly Ala Thr Ser Ala Thr Gly Gly Ala
1               5                   10                  15

Ser Gly Thr Gly
            20

<210> SEQ ID NO 24
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 24
actggtgcta gtggtgctac tagtagtggt agtagtagt                             39

<210> SEQ ID NO 25
<211> LENGTH: 13
<212> TYPE: PRT
<213> ORGANISM: Artificial
<220> FEATURE:
<223> OTHER INFORMATION: Linker region amino acid sequence

<400> SEQUENCE: 25

Thr Gly Ala Ser Gly Ala Thr Ser Ser Gly Ser Ser Ser
1               5                   10

<210> SEQ ID NO 26
<211> LENGTH: 31
<212> TYPE: DNA
<213> ORGANISM: Artificial
<220> FEATURE:
<223> OTHER INFORMATION: VH domain forward primer, chemically
      synthesized

<400> SEQUENCE: 26
cctgcatgct ggaggtgcag ttggtggaat c                                     31

<210> SEQ ID NO 27
<211> LENGTH: 23
<212> TYPE: DNA
```

```
<213> ORGANISM: Artificial
<220> FEATURE:
<223> OTHER INFORMATION: VH domain reverse primer, chemically
      synthesized
<220> FEATURE:
<221> NAME/KEY: misc_feature
<222> LOCATION: (1)..(3)
<223> OTHER INFORMATION: "asy" can appear from 1 to 50 times before the
      remainder of the sequence

<400> SEQUENCE: 27
asyagaggag acggtgacca tga                                            23

<210> SEQ ID NO 28
<211> LENGTH: 32
<212> TYPE: DNA
<213> ORGANISM: Artificial
<220> FEATURE:
<223> OTHER INFORMATION: VH domain reverse primer, first reaction,
      chemically synthesized

<400> SEQUENCE: 28
asyasyasya syagaggaga cggtgaccat ga                                  32

<210> SEQ ID NO 29
<211> LENGTH: 47
<212> TYPE: DNA
<213> ORGANISM: Artificial
<220> FEATURE:
<223> OTHER INFORMATION: VH domain reverse primer, second reaction,
      chemically synthesized

<400> SEQUENCE: 29
asyasyasya syasyasyas yasyasyaga ggagacggtg accatga                  47

<210> SEQ ID NO 30
<211> LENGTH: 22
<212> TYPE: DNA
<213> ORGANISM: Artificial
<220> FEATURE:
<223> OTHER INFORMATION: VL domain forward primer, chemically
      synthesized
<220> FEATURE:
<221> NAME/KEY: misc_feature
<222> LOCATION: (1)..(3)
<223> OTHER INFORMATION: "rst" can appear from 1 to 50 times before the
      remainder of the sequence

<400> SEQUENCE: 30
rstcagtctg ccctgactca gt                                             22

<210> SEQ ID NO 31
<211> LENGTH: 34
<212> TYPE: DNA
<213> ORGANISM: Artificial
<220> FEATURE:
<223> OTHER INFORMATION: VL domain reverse primer, chemically
      synthesized

<400> SEQUENCE: 31
caccctaggt caaccaagga cggtcaggtt ggtc                                34

<210> SEQ ID NO 32
<211> LENGTH: 37
<212> TYPE: DNA
<213> ORGANISM: Artificial
<220> FEATURE:
<223> OTHER INFORMATION: VL domain forward primer, first reaction,
      chemically synthesized
```

```
<400> SEQUENCE: 32
rstrstrstr strstrstca gtctgccctg actcagt                          37

<210> SEQ ID NO 33
<211> LENGTH: 46
<212> TYPE: DNA
<213> ORGANISM: Artificial
<220> FEATURE:
<223> OTHER INFORMATION: VL domain forward primer, second reaction,
      chemically synthesized

<400> SEQUENCE: 33
rstrstrstr strstrstrs trstrstcag tctgccctga ctcagt                46

<210> SEQ ID NO 34
<211> LENGTH: 15
<212> TYPE: DNA
<213> ORGANISM: Artificial
<220> FEATURE:
<223> OTHER INFORMATION: Linker region nucleotide sequence, chemically
      synthesized

<400> SEQUENCE: 34
ggtgctggtg gtggt                                                  15

<210> SEQ ID NO 35
<211> LENGTH: 5
<212> TYPE: PRT
<213> ORGANISM: Artificial
<220> FEATURE:
<223> OTHER INFORMATION: Linker region amino acid sequence

<400> SEQUENCE: 35

Gly Ala Gly Gly Gly
1               5

<210> SEQ ID NO 36
<211> LENGTH: 30
<212> TYPE: DNA
<213> ORGANISM: Artificial
<220> FEATURE:
<223> OTHER INFORMATION: Linker region nucleotide sequence, chemically
      synthesized

<400> SEQUENCE: 36
actggtggtg gtggtggtag tggtggtggt                                  30

<210> SEQ ID NO 37
<211> LENGTH: 10
<212> TYPE: PRT
<213> ORGANISM: Artificial
<220> FEATURE:
<223> OTHER INFORMATION: Linker region amino acid sequence

<400> SEQUENCE: 37

Thr Gly Gly Gly Gly Gly Ser Gly Gly Gly
1               5                   10

<210> SEQ ID NO 38
<211> LENGTH: 36
<212> TYPE: DNA
<213> ORGANISM: Artificial
<220> FEATURE:
<223> OTHER INFORMATION: Linker region nucleotide sequence, chemically
      synthesized
```

```
<400> SEQUENCE: 38
actactacta ctgctactac tgctggtagt ggtgct                           36

<210> SEQ ID NO 39
<211> LENGTH: 12
<212> TYPE: PRT
<213> ORGANISM: Artificial
<220> FEATURE:
<223> OTHER INFORMATION: Linker region amino acid sequence

<400> SEQUENCE: 39

Thr Thr Thr Thr Ala Thr Thr Ala Gly Ser Gly Ala
1               5                   10

<210> SEQ ID NO 40
<211> LENGTH: 15
<212> TYPE: DNA
<213> ORGANISM: Artificial
<220> FEATURE:
<223> OTHER INFORMATION: Linker region nucleotide sequence, chemically
      synthesized

<400> SEQUENCE: 40
gctactactg gtgct                                                  15

<210> SEQ ID NO 41
<211> LENGTH: 5
<212> TYPE: PRT
<213> ORGANISM: Artificial
<220> FEATURE:
<223> OTHER INFORMATION: Linker region amino acid sequence

<400> SEQUENCE: 41

Ala Ser Thr Gly Ala
1               5

<210> SEQ ID NO 42
<211> LENGTH: 24
<212> TYPE: DNA
<213> ORGANISM: Artificial
<220> FEATURE:
<223> OTHER INFORMATION: Linker region nucleotide sequence, chemically
      synthesized

<400> SEQUENCE: 42
agtactggta gtagtggtgc tggt                                        24

<210> SEQ ID NO 43
<211> LENGTH: 8
<212> TYPE: PRT
<213> ORGANISM: Artificial
<220> FEATURE:
<223> OTHER INFORMATION: Linker region amino acid sequence

<400> SEQUENCE: 43

Ser Thr Gly Ser Ser Gly Ala Gly
1               5

<210> SEQ ID NO 44
<211> LENGTH: 21
<212> TYPE: DNA
<213> ORGANISM: Artificial
<220> FEATURE:
<223> OTHER INFORMATION: Linker region nucleotide sequence, chemically
      synthesized
```

-continued

```
<400> SEQUENCE: 44
gctagtagtg gtgctagtgc t                                             21

<210> SEQ ID NO 45
<211> LENGTH: 7
<212> TYPE: PRT
<213> ORGANISM: Artificial
<220> FEATURE:
<223> OTHER INFORMATION: Linker region amino acid sequence

<400> SEQUENCE: 45

Ala Ser Ser Gly Ala Ser Ala
1               5

<210> SEQ ID NO 46
<211> LENGTH: 39
<212> TYPE: DNA
<213> ORGANISM: Artificial
<220> FEATURE:
<223> OTHER INFORMATION: Linker region nucleotide sequence, chemically
      synthesized

<400> SEQUENCE: 46
gctagtggtg gtactgctgg tactggtggt agtagtact                          39

<210> SEQ ID NO 47
<211> LENGTH: 13
<212> TYPE: PRT
<213> ORGANISM: Artificial
<220> FEATURE:
<223> OTHER INFORMATION: Linker region amino acid sequence

<400> SEQUENCE: 47

Ala Ser Gly Gly Thr Ala Gly Thr Gly Gly Ser Ser Thr
1               5                   10

<210> SEQ ID NO 48
<211> LENGTH: 51
<212> TYPE: DNA
<213> ORGANISM: Artificial
<220> FEATURE:
<223> OTHER INFORMATION: Linker region nucleotide sequence, chemically
      synthesized

<400> SEQUENCE: 48
actagtggta gtggtgctag tgctgctgct ggtggtgctg ctgctagtgc t            51

<210> SEQ ID NO 49
<211> LENGTH: 17
<212> TYPE: PRT
<213> ORGANISM: Artificial
<220> FEATURE:
<223> OTHER INFORMATION: Linker region amino acid sequence

<400> SEQUENCE: 49

Thr Ser Gly Ser Gly Ala Ser Ala Ala Ala Gly Gly Ala Ala Ala Ser
1               5                   10                  15

Ala

<210> SEQ ID NO 50
<211> LENGTH: 24
<212> TYPE: DNA
<213> ORGANISM: Artificial
<220> FEATURE:
<223> OTHER INFORMATION: Duplex with bubble, upper sequence, chemically
      synthesized
```

```
<400> SEQUENCE: 50
rstrstrstr strstrstca tgcc                                           24

<210> SEQ ID NO 51
<211> LENGTH: 24
<212> TYPE: DNA
<213> ORGANISM: Artificial
<220> FEATURE:
<223> OTHER INFORMATION: Duplex with bubble, lower sequence, chemically
      synthesized

<400> SEQUENCE: 51
ggcatgasya syasyasyas yasy                                           24

<210> SEQ ID NO 52
<211> LENGTH: 5
<212> TYPE: PRT
<213> ORGANISM: Artificial
<220> FEATURE:
<223> OTHER INFORMATION: Linker region amino acid sequence, Gly4Ser

<400> SEQUENCE: 52

Gly Gly Gly Gly Ser
1               5
```

CREATION OF VARIABLE LENGTH AND SEQUENCE LINKER REGIONS FOR DUAL-DOMAIN OR MULTI-DOMAIN MOLECULES

FIELD OF THE INVENTION

This invention in the field of molecular biology relates to libraries of dual-domain nucleic acids and/or proteins in which the domains are joined by a library of linkers that vary in length and sequence.

BACKGROUND OF THE INVENTION

Dual-domain polypeptides or dual-domain nucleic acids encoding such polypeptides may have new, advantageous properties compared to the original polypeptides or nucleic acids after which they are patterned. Such polypeptide domains are generally linked using a linker region or linker domain. A generic designation of such a polypeptide construct is $D_1$-L-$D_2$, wherein $D_1$ and $D_2$ are two structural domains that are identical or different and L is the linker. For example, two cytosolic domains of the membrane-spanning protein adenylyl cyclase coupled with a linker domain form a soluble protein (Tang et al., *Science*, 268: 1769-1772 (1995)). An advantage of this soluble form of adenylyl cyclase, which retains enzymatic activity, is that it can be produced in much higher quantities than the native enzyme (Dessauer et al., *J. Biol. Chem.*, 16967-16974 (1996)).

Another type of polypeptide generated by linking two domains is a single chain antibody or scFv. These single chain polypeptides include the variable (V) regions from the heavy (H) and light (L) chains of a selected immunoglobulin (Ig) and recreate the antigen binding site of the native Ig while being a fraction of its size (Skerra, A. et al. (1988) *Science*, 240: 1038-1041; Pluckthun, A. et al. (1989) *Methods Enzymol.* 178: 497-515; Winter, G. et al. (1991) *Nature*, 349: 293-299); Bird et al. (1988) *Science* 242:423; Huston et al. (1988) *Proc. Natl. Acad. Sci. USA* 85:5879; U.S. Pat. Nos. 4,704,692, 4,853,871, 4,946,778, 5,260,203, 5,455,030. A number of U.S. patents and international patent publications of J. Huston and colleagues describe various two chain or two domain proteins, including single chain antibodies, joined by linker peptides and optionally including cleavable sites (U.S. Pat. Nos. 5,888,773, 5,877,305, 5,861,156, 5,837,846, 5,753,204, 5,534,254, 5,525,491, 5,482,858, 5,476,786, 5,330,902, 5,302,526, 5,258,498, 5,132,405, 5,091,513, 5,013,653, WO 9323537A1 (25 Nov. 1993)

An scFv is composed of a $V_H$ domain at its N-terminus and a $V_L$ domain at its C-terminus (or vice versa) linked by a peptide linker. Correct folding of the $V_H$ and $V_L$ regions is crucial for retention of antigen binding capacity by the scFv. The length and sequence of the linker region are critical parameters for correct folding and biological function. scFv chains are easier to express than the larger Fv fragments or even larger Ig molecules (which are four chain complexes).

A ribozyme is a catalytic RNA molecule that cleaves other RNA molecules that contain nucleic acid sequences complementary to particular targeting sequences in the ribozyme. Two identical or different nucleic acid domains such as two ribozyme domains can be joined to create a bifunctional ribozyme that can act on more than one RNA substrate structure. General methods for constructing ribozymes, including hairpin ribozymes, hammerhead ribozymes and RNAse P ribozymes are known in the art. Castanotto et al. (1994) *Advances in Pharmacology*, 25: 289-317, reviews ribozymes (including group I, hammerhead, axhead, hairpin and RNAse P). Ribozymes that can advantageously target desired specific sequences, such as HIV sequences, have been described (Ho, A. et al., WO 9426877 (1994); Yu et al. (1993) *Proc. Natl. Acad. USA*, 90:6340-6344, and propulic et al. (1992) *J. Virol.*, 66:1432-1441).

The hammerhead ribozyme and the hairpin ribozyme are catalytic molecules with antisense and endoribonucleotidase activity. Their intracellular expression can confer significant resistance to, for example, HIV infection. Hammer head ribozymes are described in Rossie et al. (1991) *Pharmac. Ther.*, 50:245-254; Forster et al. (1987) *Cell*, 48:211-220; Uhlenbeck, O C (1987) *Nature*, 328:596-600; Haseloff, J. et al. (1988) *Nature*, 334:334:585; propulic et al., supra; and Castanotto et al., supra, and references cited therein. Hairpin ribozyme are disclosed in Hampel et al. (1990) *Nucl. Acids Res.*, 18:299-304; Hampel et al., EP 0360257 (1990); Haseloff, J. P. et al., U.S. Pat. No. 5,254,678 (1993); Kraus, G. et al., U.S. Pat. No. 5,958,768 (1999); Ho, A. et al., WO 9426877 (1994); Ojwang et al. (1992) *Proc. Natl. Acad. USA*, 89: 10802-10806; Yamada et al. (1994) *Gene Therapy* 1: 39-45; Leavitt et al. (1995) *Proc. Natl. Acad. USA*, 92: 699-703; Leavitt et al., *Human* Gene Therapy, 5: 1151-1120; and Yamada et al. (1994) *Virology*, 205: 121-126).

For convenience, the conventional single letter nucleotide code to designate positions wherein more than one base may be present is provided in Table 1.

TABLE 1

| | For RNA | For DNA | |
|---|---|---|---|
| r = | g or a | g or a | (purine) |
| y = | u or c | t or c | (pyrimidine) |
| s = | g or c | g or c | |
| w = | a or u | a or t | |
| v = | a, g or c | a, g or c | |
| x = | c, u, or a | c, t, or a | |
| n = | a, g, c, or u | a, g, c, or t | |

(Obviously, in an r:y pairing, if r = g then y = c, etc.)

The typical substrate sequence for hairpin ribozymes is nnng/cn*gucnnnnnnnn (where n*g is the cleavage site). The hammerhead ribozyme cleaves at any nux sequence. Thus, the same substrate target within the hairpin leader sequence, guc, is targetable by the hammerhead ribozyme.

Two DNA domains can be also linked to form a dual-domain DNA molecule. Certain DNA domains bind to proteins such as DNA polymerases, endonucleases, and transcription factors. Thus, two linked DNA domains can be linked to form a dual-domain DNA molecule that binds one or more DNA binding protein.

Those skilled in the art will know of the existence of other nucleic acid or polypeptide domains that may be advantageously linked to form a dual-domain nucleic acid or polypeptide with one or more functions. Those of skill will also recognize the general desirability of methods that yield such products.

The desired property of a dual-domain DNA, ribozyme or protein molecule can be optimized by modifying the nucleic acid that (1) constitutes the DNA domain, (2) encodes the ribozyme sequence or (3) encodes the protein domain. This is achieved through a variety of conventional techniques. In one approach, the sequence or length of the linker region is varied in an effort to optimize the dual-domain molecule. The length and sequence of the linker region may indeed be critical to the function of a dual-domain protein.

Methods for generating a scFv dual-domain protein with linkers of varying peptide length are known in the art (e.g., U.S. Pat. No. 5,837,242). Changes in sequence or length of the linker can adversely affect the stability, protease susceptibility, binding activity and expression levels of the scFv. Because, the effect of a change in linker sequence or length on the function(s) of the dual-domain polypeptide has been generally unpredictable, the effect on bioactivity of varying particular amino acid residues in the linker or changing its overall length generally cannot be determined a priori.

There is thus a need for methods that permit creation of a nucleic acid library that encodes $D_1$-L-$D_2$ (or higher order) structures wherein L has random length and sequence. The dual-domain protein can be expressed from the library and the properties of interest can be analyzed. Once a protein is identified as having "optimal" properties, its sequence can be determined by resolving the nucleotide sequence of the clone that encodes that protein. This approach obviates the necessity of creating and testing individual clones until finding one with the desired property.

The polymerase chain reaction (PCR) has been used to generate libraries of nucleic acid products that have two domains connected by a linker having different sequences or different lengths. No currently available method permits simultaneous introduction of both random length and random sequence into the linker region of a population of nucleic acids.

Expression Systems

Many expression systems for heterologous proteins are known in the art. These include bacterial systems which have the advantages of rapid and abundant production, but are limited in many instances by their inability to produce properly folded and soluble proteins (unless the proteins are subjected to cycles of denaturation and renaturation). Baculovirus systems drive expression through the secretory pathways of insect cells, thereby increasing the probability of improved protein solubility (Kretzschmar, T. et al. (1996) *J. Immunol. Methods* 195:93-101; Brocks, B. et al. (1997), *Immunotechnology* 3:173-184). Because manipulating the virus and growing insect cells can be time consuming and costly, the system is less suitable for expression of certain types of proteins, for example tumor-specific or individual-specific proteins such as idiotypic scFv polypeptides. There is therefore a need in the art for suitable rapid and economical expression systems to produce useful dual-domain proteins, one example of which is an idiotypic scFv vaccine for treating B-cell lymphoma. The present invention addresses this need.

SUMMARY OF THE INVENTION

The present invention inventors have conceived of an approach for generating a library of dual-domain or multi-domain (>2) polypeptides from appropriate coding nucleic acids, which library is characterized by the members having random linkers linking each pair of polypeptide domains, wherein the random linkers have variable length and sequence. The nucleotide sequences encoding the linkers comprise a repeated pattern of degenerate triplet bases. The first and second (and/or higher order) domains may be the same or different from one another. The amino acid composition of an entire linker region may include between 1 and about 20 different amino acids with each repeated pattern of degenerate triplet bases encoding between 1 and about 12 different amino acids. The preferred linker length ranges from 1 to 50 amino acids. In one embodiment, the polypeptide is a single chain immunoglobulin or single chain antibody (scFv) molecule wherein one domain is an immunoglobulin $V_H$ domain and the other domain is an immunoglobulin $V_L$ domain.

More specifically, the present invention is directed to a library of dual-domain nucleic acid molecules each of which has (a) a first and a second domain; (b) separating and linking the domains, a linker which is a member of a randomized library of linkers that (i) vary in size and nucleotide sequence, (ii) consist of a repeated pattern of degenerate repeated triplet nucleotides.

In the above library, the repeated pattern of degenerate repeated triplet nucleotides of the linkers have the following properties:

(i) position 1 of each repeated triplet cannot be the same nucleotide as position 2 of the repeated triplet; or
(ii) position 2 of each repeated triplet cannot be the same nucleotide as position 3 of the repeated triplet; or
(iii) position 1 of each repeated triplet cannot be the same nucleotide as position 3 of the repeated triplet.

Preferably, the nucleotide in the first and second positions of each repeated triplet is selected from any two of deoxyadenosine, deoxyguanosine, deoxycytidine or deoxythymidine. In another embodiment, (i) position 1 of each repeated triplet is deoxyadenosine or deoxyguanosine; (ii) position 2 of each repeated triplet is deoxycytidine or deoxyguanosine; and (iii) position 3 of each repeated triplet is deoxythymidine.

In another embodiment, two different repeated patterns of degenerate triplet bases are combined to generate a population of linkers used to produce dual-domain molecules. The combination of different repeated patterns of degenerate triplet bases is used to increase the complexity of the linker sequences obtained from the population. The different repeats can also be used to introduce differing structural or biochemical properties to the linker region. For example, degenerate triplet vwc and degenerate triplet nvt are used as the nontemplated sequence. In this example, the degenerate linker sequence is $(vwc)_x(nvt)_y$, where x=1 to 20 and y=1 to 20. This combination would produce linkers containing different combinations of amino acids within each repeat as well as differing length of linkers.

In one embodiment of the above library, at least one of the domains binds to a protein. In another embodiment, both of the domains bind to a protein.

In yet another embodiment, at least one, preferably both, of the domains binds to a nucleic acid that is not a member of the library.

In any of the above nucleic acid libraries, the first and the second domains are preferably coding sequences.

The library, as described above, is preferably produced in plants or plant cells.

The present invention also provides a dual-domain or multi-domain nucleic acid molecule selected out from the library described above.

Also provide is a library of dual-domain polypeptide molecules each of which is described by the formula $D_1$-L-$D_2$ (going from N-terminus to C-terminus) wherein (a) $D_1$ and $D_2$ are polypeptide domains and
(b) L is a peptide or polypeptide linker which is a member of a randomized library of linkers that vary in size and sequence, which library is encoded by nucleic acid sequences consisting of a repeated pattern of degenerate repeated triplet nucleotides.

In a preferred embodiment, the present invention is directed to a library of multi-domain polypeptide molecules each of which comprises polypeptide domains D, each pair of D's being linked by a peptide or polypeptide linker L, such that each molecule is described by the formula $$D_x L_y$$

wherein x is an integer between 2 and about n, wherein n is preferably about 20, y is an integer between 1 and (n−1), with the proviso that for any value of x, y is preferably x−1; $D_1$ is bonded to a single C-terminal linker; $D_n$ (the "ultimate" C-terminal domain) is bonded to a single N-terminal linker; each of $D_2$ to $D_{n-1}$ are bonded to a N-terminal and a C-terminal linker; each L is a member of a randomized library of linkers that vary in size and sequence, which linker library is encoded by nucleic acid sequences consisting of a repeated pattern of degenerate repeated triplet nucleotides.

A preferred library is a library of dual-domain polypeptide molecules each of which is described by the formula $D_1$-L-$D_2$ wherein
  (a) $D_1$ and $D_2$ are polypeptide domains and
  (b) L is a peptide or polypeptide linker which is a member of a randomized library of linkers that vary in size and sequence, which library is encoded by nucleic acid sequences consisting of a repeated pattern of degenerate repeated triplet nucleotides.

In the above libraries of dual- or multi-domain polypeptide molecules, each linker in the library preferably (i) has a length of between about 1 and 50 amino acid residues and (ii) consists of between 1 and about 20 different amino acids and (iii) each repeated pattern of degenerate triplet bases encodes between 1 and 12 different amino acids.

In the library of dual domain or multi-domain polypeptide molecules above, the repeated pattern of degenerate repeated triplet nucleotides encoding the linkers preferably has the following properties:
  (i) position 1 of each repeated triplet cannot be the same nucleotide as position 2 of the repeated triplet; or
  (ii) position 2 of each repeated triplet cannot be the same nucleotide as position 3 of the repeated triplet; or
  (iii) position 1 of each repeated triplet cannot be the same nucleotide as position 3 of the repeated triplet.

Preferably, the nucleotide in the first and second positions of each repeated triplet is selected from any two of deoxyadenosine, deoxyguanosine, deoxycytidine or deoxythymidine. In one embodiment thereof (i) position 1 of each repeated triplet is deoxyadenosine or deoxyguanosine; (ii) position 2 of each repeated triplet is deoxycytidine or deoxyguanosine; and (iii) position 3 of each repeated triplet is deoxythymidine.

The above library of dual- or multi-domain polypeptides is preferably produced in plant cells.

Specific embodiments of this invention include any dual-domain (or multi-domain) polypeptide molecule selected from the library as described above. One embodiment provides a three domain peptide selected from the above library which is a dual domain scFv polypeptide linked to a third polypeptide domain. third domain is preferably a toxin polypeptide with therapeutic utility or an enzyme with diagnostic utility or use as a research tool. The foregoing polypeptides are preferably produced in plant cells.

This invention is further directed to a method for generating the library of dual-domain nucleic acids as above, comprising:
a. obtaining two template DNA sequences that comprises the first and the second domains;
b. preparing amplification primer pairs which amplify the first and second domains where each primer pair comprises an upstream primer and a downstream primer, each primer having a 5' end and a 3' end, wherein the downstream primer for the first domain or the upstream primer for the second domain comprises a nontemplated sequence,
   the nontemplated sequence comprising a repeated pattern of degenerate repeated triplet nucleotides, wherein at least two of the 5' terminal triplets of the repeated pattern of degenerate repeated triplet nucleotides have the same degenerate sequence;
c. amplifying the domains with the amplification primers to generate at least one population of nucleic acid domains having different lengths and sequences in the non-templated sequence; and
d. ligating the nucleic acid domains generated in step (c) to generate the a population of dual-domain molecules.

In the above method, the repeated pattern of degenerate repeated triplet nucleotides in at least one of the primers preferably has the following properties:
  (i) position 1 of each repeated triplet cannot be the same nucleotide as position 2 of the repeated triplet; or
  (ii) position 2 of each repeated triplet cannot be the same nucleotide as position 3 of the repeated triplet; or
  (iii) position 1 of each repeated triplet cannot be the same nucleotide as position 3 of the repeated triplet.

In one embodiment of the above libraries of dual- or multi-domain polypeptide molecules, a linker in the library that consists of 10 or more residues in length should contain at least three different residues and a linker in the library that consists of 20 or more residues in length should contain at least four different residues.

In the above method, at least one of the primers preferably contains a non-templated endonuclease recognition site.

In the foregoing methods, the template DNA sequences are preferably made by reverse transcription of mRNA.

The method may further comprise the step of ligating the population of dual-domain nucleic acids to vectors, and, further comprise the step of introducing the vector into a host. In these methods, the nucleic acid domains generally will encode polypeptide domains, and the method preferably also comprises the step of expressing dual-domain polypeptides encoded by the dual-domain nucleic acids. In an additional step, the method may comprise the step of transcribing RNA from the vectors.

For plant expression, the vectors should be compatible with replication and/or expression of the nucleic acids in plant cells. The method preferably includes the steps of introducing the transcribed the RNA into a plant cell and expressing the dual-domain (or multi-domain) polypeptide.

This invention also provides a population of dual-domain polypeptides or a dual-domain polypeptide selected from that population, produced by the method described above. Preferably the population or selected polypeptide is produced in plant cells.

Also provided is a method of producing a dual domain (or, with appropriate modifications, a multi-domain) polypeptide, comprising the steps of:
(a) joining a nucleic acid encoding the first domain of the polypeptide to a nucleic acid encoding a first part of a linker to produce a first nucleic acid construct;
(b) joining the nucleic acid encoding a second part of the linker to a nucleic acid encoding the second domain of the polypeptide to produce a second nucleic acid construct;
(c) incorporated the first and the second constructs into a transient plant expression vector in frame so that, when expressed, the polypeptide bears the first and second domain separated by the linker as described by the formula $D_1$-L-$D_2$.

(d) transfecting a plant (or plant cell) with the vector so that the plant transiently produces the polypeptide; and (e) recovering the polypeptide as a soluble, functionally-folded protein.

General References

Unless otherwise indicated, the practice of many aspects of the present invention employs conventional techniques of molecular biology, recombinant DNA technology and immunology, which are within the skill of the art. Such techniques are described in more detail in the scientific literature, for example, Sambrook, J. et al., *Molecular Cloning: A Laboratory Manual*, 2nd Ed., Cold Spring Harbor Press, Cold Spring Harbor, N.Y., 1989, Ausubel, F. M. et al. *Current Protocols in Molecular Biology*, Wiley-Interscience, New York, current volume; Albers, B. et al., *Molecular Biology of the Cell*, $2^{nd}$ Ed., Garland Publishing, Inc., New York, N.Y. (1989); Lewin, B M, Genes IV, Oxford University Press, Oxford (1990); Watson, J. D. et al., *Recombinant DNA*, Second Edition, Scientific American Books, New York, 1992; Darnell, J O E et al., *Molecular Cell Biology*, Scientific American Books, Inc., New York, N.Y. (1986); Old, R. W. et al., *Principles of Gene Manipulation: An Introduction to Genetic Engineering*, $2^{nd}$ Ed., University of California Press, Berkeley, Calif. (1981); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition); *Methods in Enzymology: Guide to Molecular Cloning Techniques* (Berger and Kimball, eds., 1987); Hartlow, E. et al., *Antibodies: A Laboratory Manual*, Cold Spring Harbor Laboratory Press, Cold Spring Harbor, N.Y., 1988), Collegian, J. E. et al., eds., *Current Protocols in Immunology*, Wiley-Interscience, New York 1991. Protein structure and function is discussed in Schulz, G E et al., *Principles of Protein Structure*, Springer-Verlag, New York, 1978, and Creighton, T E, *Proteins: Structure and Molecular Properties*, W.H. Freeman & Co., San Francisco, 1983.

Definitions

As used herein, the following terms have the meanings ascribed to them unless specified otherwise.

A polypeptide or protein "domain" generally refers to a region of a polypeptide chain that is folded in such a way that confers a particular structure and/or biochemical function. (Schulz et al., supra). Domains can be defined in structural or functional terms. A functional domain can be a single structural domain, but may also include more than one structural domain. Such functions can include enzymatic catalytic activity, ligand binding, chelating of an atom or endogenous fluorescence. As discussed above, and of particular importance to this invention, $V_H$ and $V_L$ regions of Ig molecules each form single structural domains, which act in concert in forming an antigen-combining site. A domain's function is dictated to a large extent by the distinct shapes into which it folds. Although most commonly used to describe proteins, a "domain" can also describe a region of a nucleic acid, either the coding sequence of a polypeptide domain, or a nucleic acid structure that carries out a particular function (e.g., a ribozyme's catalytic activity or protein binding). Binding domains, defined by binding to a binding partner (receptor or ligand) are exemplified by the $V_H$ and $V_L$ regions of Ig molecules (see below), each of which forms a single structural domain that act in concert in forming an antigen-combining site. Other well-known binding domains are extracellular domains of cell surface receptors that bind a respective ligand, for example, a peptide hormone. Moreover, the portions of a polypeptide or peptide ligand such as erythropoietin, GM-CSF or enkephalin, that binds to its respective receptor is considered a functional (binding) domain. Parts of proteins that are responsible for the capacity to fluoresce (e.g., green fluorescent protein—GFP) are also considered functional domains.

A binding domain of a DNA or RNA molecule is a part of the molecule that binds a protein (preferably) such as a transcription factor (e.g., cAMP Response Element Binding Protein (CREB)), a restriction enzyme (e.g., EcoR I) or a DNA polymerases (e.g., Taq DNA Polymerase).

The present invention is directed in part to methods for creating dual-domain molecules. In preferred dual-domain molecules, the linker regions between the two domains is varied whereas the sequence of the linked domains is held constant.

"Template DNA" refers to the DNA that is amplified by "amplification primer pairs" (the population of oligonucleotide primers used in the amplification reaction). This DNA may be produced by biological (recombinant) or synthetic (chemical) means. Further, mRNA may be reverse transcribed to form the template DNA that is used in the amplification reaction.

An "upstream primer" is an oligonucleotide primer, or a mixture of oligonucleotide primers, that anneal(s) to the antisense strand of the template DNA.

A "downstream primer" is an oligonucleotide primer, or a mixture of oligonucleotide primers, that anneal(s) to the sense strand of the template DNA.

A "nontemplated sequence" is the portion of an amplification primer that contains a repeated nucleotide triplet. As the goal of this sequence is to introduce variability into the linker library, it is not complementary to the DNA sequence being amplified, e.g., the polypeptide domain-coding regions.

The phrase "repeated pattern of degenerate triplet bases" refers to a nucleic acid sequence wherein a set of three bases (a triplet) is repeated in the nontemplated sequence, creating a repeating motif where the individual bases in the repeating triplet are independently selected from a defined array. For example, where the repeated triplet is nws (see Table 1), n can be any of a, c, g, or t; w can be a or t, and s can be 9 or c, rendering the repeated pattern degenerate. Herein, these repeated triplets are adjacent to each other. The nontemplated sequence of the amplification primer that contains these "repeated pattern of degenerate triplet bases" is produced in vitro.

"Amplifying/amplification" refers to a reaction wherein the entire template DNA, or portions thereof, are duplicated at least once, preferably many times.

"Ligating/ligation" refers to covalent coupling of two or more DNA strands (3' end to 5' end) using enzymatic and/or chemical methods.

A "nontemplated endonuclease recognition site" is a sequence within the nontemplated sequence that is recognized by a restriction endonuclease.

One use of the term "library" herein refers to a population, set or collection of nucleic acid molecules consisting of domains joined by linker sequences, which linkers vary in size and nucleotide sequence and which are produced using the methods described. The number of library members contained in the library which differ in nucleotide sequence is determined by the number of sequences contained in the repeated pattern of degenerate triplet bases. The term "library" is also applied to the population of polypeptides encoded by the nucleic acid library.

As used herein, a "linker" at the nucleic acid level is a nucleic acid molecule or sequence that joins two nucleic acid domains or two nucleic acid sequences encoding two polypeptide domains. The linker sequence has a pattern of degenerate repeated triplet nucleotides with the following properties:
(i) position 1 of each repeated triplet cannot have the same nucleotide as at position 2 of the repeated triplet; or
(ii) position 2 of each repeated triplet cannot be the same nucleotide as position 3 of the repeated triplet; or
(iii) position 1 of each repeated triplet cannot be the same nucleotide as position 3 of the repeated triplet.

At the protein level, the linker is the peptide expression product of the linker nucleic acid sequence. In a preferred embodiment, the present linker excludes such sequences that encode (or are) $Gly_4Ser$ or repeats thereof.

As used herein, a "library of linkers" (or "linker library") at the nucleic acid level is a set or collection or population of nucleic acid molecules or sequences each of which joins two nucleic acid domains or two nucleic acid sequences encoding two polypeptide domains, each library member of which has a pattern of degenerate repeated triplet nucleotides with the following properties:
(i) position 1 of each repeated triplet cannot have the same nucleotide as at position 2 of the repeated triplet; or
(ii) position 2 of each repeated triplet cannot be the same nucleotide as position 3 of the repeated triplet; or
(iii) position 1 of each repeated triplet cannot be the same nucleotide as position 3 of the repeated triplet.

At the protein level, the linker library is the set of expression products of the population of linker nucleic acid members of the library.

A "single-chain antibody" (scFv; also termed "scAb" by others) is a single chain polypeptide molecule wherein an Ig heavy chain variable ($V_H$) domain and an Ig light chain variable ($V_L$) domain are artificially linked by a relatively short peptide linker that allows the scFv to assume a conformation which retains binding capacity and specificity and for the antigen (or epitope) against which the original antibody (from which the $V_H$ and $V_L$ domains are derived) was specific.

DESCRIPTION OF THE PREFERRED EMBODIMENTS

Figure 1:
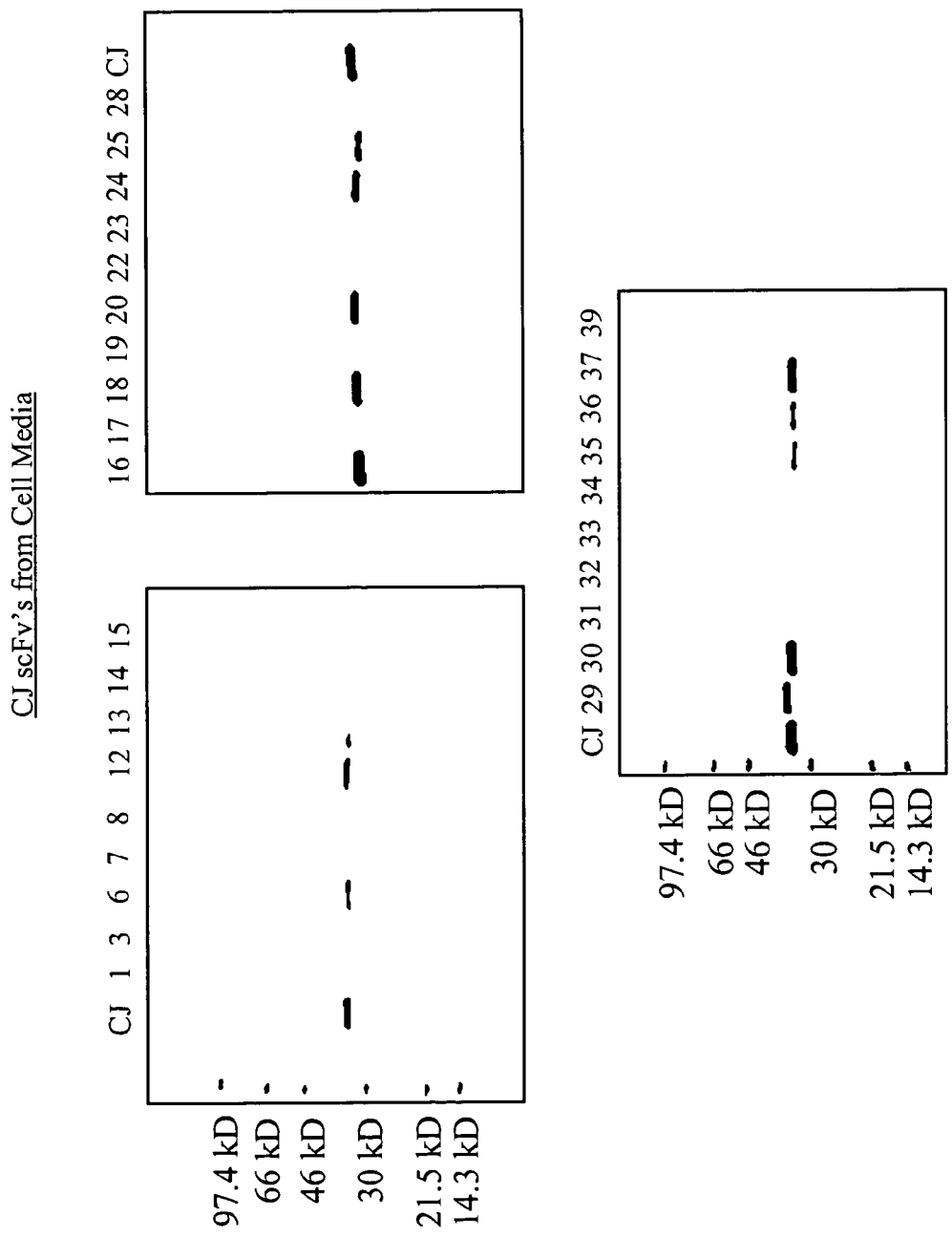
Figure 2:
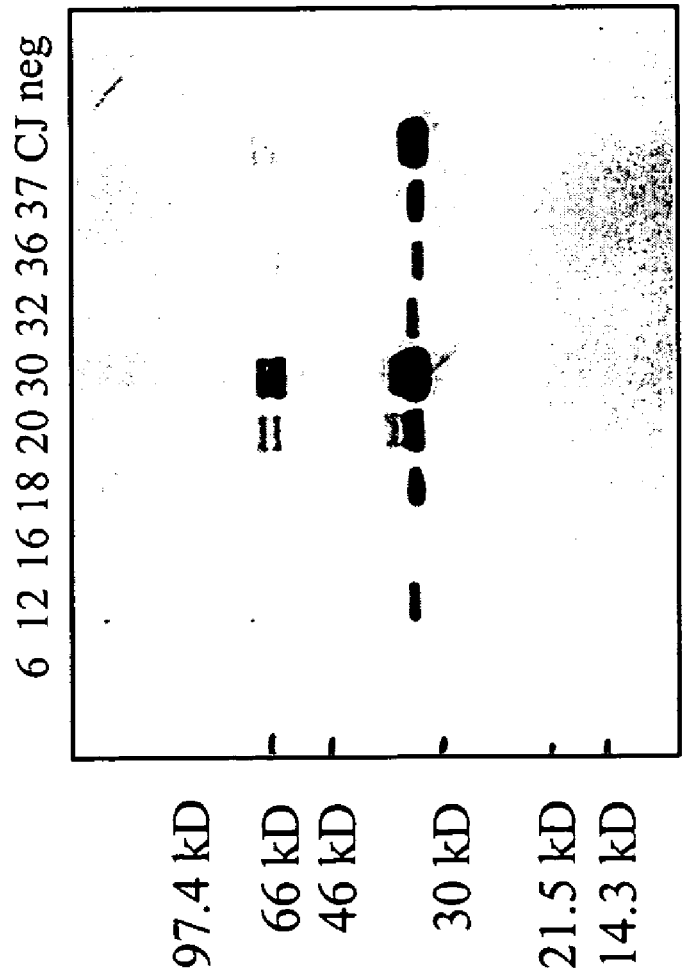
FIG. 2 shows a Western blot analysis of scFv proteins generated in Example 2 in whole plants. CJ is the scFv with the $(Gly_4Ser)_3$ SEQ ID NO: 3 linker. The number of the lane refers to the # of the clone. The size in kDa is shown on the left.

The present invention employs expression systems, preferably plant-based, to produce dual-domain proteins, for example, individualized tumor-specific immunogens for treating B cell lymphoma. The plant-based transient heterologous expression system described herein produces correctly folded polypeptides in surprisingly high abundance and with surprisingly potent immunogenicity. This system allows rapid and economical production of useful quantities of such proteins or polypeptides.

The nucleic acid encoding the dual-domain product is introduced into plants using an appropriate plant virus vector, described in detail below, leading to expression and rapid production of appropriately folded dual-domain protein in plant cells, plant parts and whole plants.

The selection of (1) appropriate linkers and (2) the transient expression system, as described herein, ensure that useful dual-domain polypeptide molecules are secreted by the plant cells in a form that is folded in solution in a conformation that permits their use for their intended purpose, e.g., as tumor-specific immunogens. An scFv produced according to this invention is advantageously obtained as the predominant secreted protein species in those plant cells into which it has been successfully incorporated. This permits simple selection and straightforward, rapid purification for the uses described herein, including as a vaccine composition.

While plant expression systems are preferred for reasons enumerated herein, the invention is not intended to be limited to any particular system. The present approaches for generation of random linker libraries of varying degrees of complexity in the production of dual domain (or multi-domain) nucleic acids and proteins can be applied to other prokaryotic and eukaryotic hosts, for example bacteria, yeast cells or mammalian cells.

In addition to the scFv vaccines comprising Ig V domains that are described below, the present invention can be applied directly to other protein antigens which can expressed in plants in a similar manner to achieve proper folding and enhanced immunogenicity. Examples include antigens that are common to a particular type of tumor or family of tumors, such as carcinoembryonic antigen (CEA), prostate-specific antigen (PSA) present in prostate adenocarcinomas, tyrosinase present in melanomas, and many other known and yet undiscovered tumor antigens. Another type of clonally-distributed (self) antigen is a T cell receptor (TCR) domain that includes a portion of the α, β, γ or δ chain V region (or a combination thereof). Such TCR-based antigens can be markers and therefore, targets in certain T cell leukemias and lymphomas as well as in autoimmune diseases. Thus, autoimmune diseases associated with identifiable T cell clones or with usage of a particular TCR chain V region are modulated/treated by immunizing with a polypeptide antigen corresponding to TCR V region polypeptides that is made by the approach described herein.

Other dual domain proteins within the scope of the invention include a viral coat protein domain combined with another domain of interest. If necessary, this molecule is purified taking advantage of the coat protein's characteristics.

The protein domains are not limited to those expressed on the cell surface; dual domain proteins wherein one or both polypeptides are derived from a cytosolic protein or a protein that functions in soluble form are also intended. Examples include cytokines such as IL-1β and polypeptide hormones.

Other preferred polypeptide domains that are linked as dual- or multi-domain proteins using the linker approach of the present invention are transcription factors. These can be assembled so that active domains of different transcription factors that act in concert or sequentially are combined as single chain molecules separated by linkers. The linker size and complexity is chosen on the basis of the functional requirements for the transcription factors, e.g., the distance between the nucleic acid binding sites for these factors if they must bind and act at about the same time. Such dual domain or multi-domain polypeptides would be expected to show advantageous properties in promoting, activating or orchestrating transcriptional events. This may be particularly useful in cases where more than one factor must act and one is limiting in its concentration or availability. This limitation is overcome by creating an artificial dual domain or multi-domain transcription factor where the domain of the otherwise limiting factor is always linked to a domain or domains or one or more nonlimiting transcription factors.

Alternatively, a transcription factor domain may be linked using the present approach to an inhibitory moiety such as a toxin so that binding of the transcription factor domain to its target DNA permits the toxin to perform its function and inhibit transcription or otherwise block a cellular function. Use of the stimulatory or inhibitory transcription factor constructs with linkers having the appropriate flexibility could permit the attainment of new levels of control over cellular functions not heretofore possible using mixtures of proteins or by protein domains that have been linked by a limited array of preselected individual linkers. The random linker library approach generates a much larger array of choices that can be selected by appropriate means as described herein.

The dual- or multi-domain polypeptides prepared in accordance with this invention using the random linker library approach can be delivered to a target cell exogenously, or can be combined in an expression system that is inserted into the target cell and functions autonomously or under the control of cellular factors. This can be accomplished using routine method of molecular biology using conventional vectors such as viral vectors that deliver the nucleic acid encoding the polypeptides to the appropriate cells by selective or nonselective means.

The product of the present invention may be used in the form of a dual (or multi) domain nucleic acid molecule, for example, a bifunctional DNA vaccine that is intended for administration to a subject and, when expressed, produces an immunogenic dual domain protein in the subject.

Unless otherwise indicated, the practice of the present invention employs conventional techniques of molecular biology, recombinant DNA technology and immunology, which are within the skill of the art. Such techniques are described in more detail in the references listed earlier.

Focusing on a linker region L between two polypeptide domains, it may be difficult to predict what amino acid substitutions or additions will optimize a particular property of the linker, and therefore, of the multi-domain polypeptide as tested. for example, in a biochemical or biological assay. The length and the sequence of L can affect the activity of the polypeptide product because of an impact on properties such as solubility, folding and conformation, protease susceptibility or expression level.

The present invention provides approaches for creating a nucleic acid library, that when expressed, results in a library of polypeptides with linker regions that are variable in both length and sequence. This invention permits a practitioner to create and analyze such libraries, thereby providing advantages over the prior art where either length or sequence, but not both, could be varied.

The present invention is based on the use of known template nucleic acids that encode the protein domains of interest. The nucleic acid encoding a first domain is amplified in a PCR reaction using an upstream primer that is complementary to the antisense strand of the template and a downstream primer that is complementary to the sense strand of the template DNA and that may contain repeated triplets of nucleotides at its 5' end.

Then the nucleic acid for the second domain is amplified in a PCR reaction with an upstream primer that is complementary to the antisense strand of the template DNA and that may have a repeated nucleotide triplet sequence at its 5' end and with a downstream primer that is complementary to the sense strand of the template DNA.

To get the desired variability in length and sequence, either the downstream primer for the first domain and/or the upstream primer for the second domain must contain the repeated triplet of nucleotides. The resulting two PCR products are then combined to form a nucleic acid that encodes a dual-domain protein, or contains the dual DNA or dual RNA domains that are linked by the linker region. This resultant molecules (protein, DNA or RNA) can then be analyzed by a variety of means known to those of skill in the art.

The structures of proteins and nucleic acids and their domains are determined by well-known biochemical and biophysical methods, in particular X-ray crystallography and two-dimensional nuclear magnetic resonance (2D-NMR) spectroscopy. Inspection of a 3D structure may be sufficient to delineated a macromolecule's domains. For example, the 3D structure of the dimeric enzyme glutathione reductase illustrates that each subunit is composed of three structural domains—a FAD binding domain, a NADP binding domain and a third domain that forms the interface between the dimers. See Schulz et al., supra. The Ig $V_H$ and $V_L$ domains cooperate to form the antibody's antigen binding pocket. Thus these structural domains fold into distinct shapes that are important for the molecule's function.

Cloning of Domains

A domain may be isolated by any of a number of techniques. In general, a nucleic acid sequence encoding a polypeptide (or RNA) domain of interest is cloned from an appropriate cDNA library or a genomic DNA library based on hybridization with a oligonucleotide probe that represents the domain.

For the present invention, preferred nucleic acids and proteins are mammalian, more preferably human sequences.

Alternatively, the DNA is isolated by amplification techniques using oligonucleotide primers starting with a DNA or RNA template. (See, e.g., Dieffenfach et al., *PCR Primer: A Laboratory Manual* (1995)). These primers can be used to amplify either a full length coding sequence or a partial sequence that could constitute a probe (ranging in length up to about several thousand nucleotides). The resultant probe sequence is then used to screen a mammalian library for the full-length nucleic acid of interest. Use of synthetic oligonucleotide primers and amplification of an RNA or DNA template is described in U.S. Pat. Nos. 4,683,195 and 4,683,202; *PCR Protocols: A Guide to Methods and Applications* (Innis et al., eds, 1990)). Methods such as PCR and ligase chain reaction (LCR) can be used to amplify nucleic acid sequences of domains directly from mRNA, from cDNA, or from genomic or cDNA libraries. Degenerate oligonucleotides can be designed to amplify domain homologues using the known sequences that encode the domain. Restriction endonuclease sites can be incorporated into the primers. Genes amplified by the PCR reaction can be purified on agarose gels and cloned into an appropriate vector.

In expression cloning, nucleic acids are isolated from expression libraries using as a probe an antibody (or other binding partner) specific for an epitope of the expressed polypeptide. Polyclonal or monoclonal antibodies (mAbs) can be raised by immunization with one or more peptide fragments of the domain being cloned.

Nucleic acid probes, preferably oligonucleotides are used under preferably stringent hybridization conditions to screen libraries in order to isolate polymorphic variants or alleles of *the* genes that encode the polypeptide domain of interest. Alternatively, antibody-based expression cloning permits cloning of polymorphic or allelic variants or interspecies homologues.

Selection of sources for the cDNA library and its production from mRNA is done using conventional methods (Gubler et al., *Gene* 25:263-269 (1983); Sambrook et al., *Molecular Cloning, A Laboratory Manual* ($2^{nd}$ ed. 1989); *Current Protocols in Molecular Biology* (Ausubel et al., eds., 1994 or latest edition).

Methods for preparing genomic DNA libraries are conventional in the art. For example, DNA extracted from a tissue may be mechanically sheared or enzymatically digested to yield fragments of about 12-20 kb that are separated by gradient centrifugation and inserted into appropriate expression vectors. These vectors are packaged into phage in vitro. Recombinant phage are analyzed by plaque hybridization (Benton et al., *Science* 196:180-182 (1977). Colony hybridization is carried out, for example, as generally described by Grunstein et al., *Proc. Natl. Acad. Sci. USA.,* 72:3961-3965 (1975).

Synthetic oligonucleotides can be used to construct recombinant "genes" for use as probes or for expression of the domain polypeptides.

Oligonucleotides can be chemically synthesized using solid phase phosphoramidite triester methods (Beaucage et al., *Tetrahedron Letts.* 22:1859-1862 (1981)) using an automated synthesizer (Van Devanter et al., *Nucleic Acids Res.* 12:6159-6168 (1984)). Purification of oligonucleotides is typically by native acrylamide gel electrophoresis or by anion-exchange HPLC (Pearson et al., *J. Chrom.* 255:137-149 (1983)).

Sequences of cloned genes and synthetic oligonucleotides can be verified by conventional methods such as the chain termination method (Wallace et al., *Gene* 16:21-26 (1981) using a series of overlapping oligonucleotides usually 40-120 bp in length, representing both the sense and antisense strands of the gene.

The nucleic acid encoding the desired polypeptide is typically cloned into an intermediate vector before transformation or transfection of prokaryotic or eukaryotic cells for replication and/or expression of the nucleic acid. These intermediate vectors, e.g., plasmids or shuttle vectors, are typically for use in prokaryotic cells.

Linker Region

Functions of the linker L are to join a first and a second polypeptide (or nucleic acid) domain as a single macromolecule, permit the two domains to fold correctly and thereby assemble into a functional molecule. In the scFv embodiment where the amino acid linker L links the $V_H$ and $V_L$ domains, L may vary in length between 1 and about 50 residues. An individual L preferably is composed of between 1 and about 20 different amino acids, and each repeated pattern of degenerate triplet bases encodes between 1 and about 12 different amino acids. An optimal linker contributes significantly to the correct folding of the $V_H$ and $V_L$ domains so that the resulting scFv (a) is soluble and (b) binds antigen or (c) is able to act as an antigen to elicit a relevant immune response.

In one embodiment the linker will be resistant to cleavage by proteases that the final product is expected to encounter when being used.

In contrast, the linker may also be designed to incorporate an amino acid or short sequence that serves as a cleavable site for a protease that can be used to separate the one or several domains from one another at an appropriate time.

Additionally, the linker may be designed to confer affinity to another molecule or matrix facilitating subsequence purification of the expressed of the fused domains based on the properties of the linker. One example includes incorporation of a histidine (His) tag that permits purification on a metal (e.g., nickel) affinity column. Other affinity tags are well-known in the art and need not be described here.

Depending on the two domains being linked, the sequence and length of L can vary widely.

Linkers may be selected based on their ability to fuse two polypeptide domains and at the same time, facilitate purification and characterization based on the properties of one (or both) domains. Examples include fusions of a selected protein domain and glutathione S-transferase (GST), which can then be purified on an affinity matrix of glutathione-agarose (Smith et al. (1988) *Gene,* 67:31-40). The linker used by Smith et al. was later modified by Guan et al. (*Anal. Biochem.* 192:262-267 (1991)) to introduce a glycine rich stretch known as a "glycine kinker" having the amino acid sequence PGISGGGGG [SEQ ID NO:1]. Such a linker, within the scope of this invention, facilitates the cleavage of GST from its fusion partner (in that example, a protein tyrosine phosphatase).

Vectors for producing these kinds of fusion proteins are well-known in the art, and many are commercially available. For example, New England Biolabs provides pMAL-p2, a vector that encodes a maltose binding protein that can be fused to a domain sequence that is cloned into the vector. In pMAL-p2, the amino acid sequence of the linker between the maltose-binding protein and the added domain is NNNNNNNNNNLGIEGR [SEQ ID NO:2]. The stretch of asparagines facilitates purification of the fusion protein on an amylose affinity column.

A linker that has been used to link Ig $V_H$ and $V_L$ domains into an scFv is the 15 amino acid sequence GGGGSGGGGSGGGGS (SEQ ID NO:3), commonly designated ($Gly_4Ser$)$_3$ SEQ ID NO: 3. A number of other linkers for scFv production have been described in Lawrence et al., *FEBS Letters,* 425: 479-484 (1998), Solar et al., *Protein Engineering,* 8:717-723 (1995), Alfthan et al, *Protein Engineering* 8: 725-731 (1995), Newton et al., *Biochemistry,* 35:545-553 (1996). Ager et al., *Human Gene Therapy,* 7: 2157-2164 (1996) and Koo et al., *Applied and Environmental Microbiology,* 64:2490-2496 (1998), The library approach of this invention will generate many useful linkers beyond those noted above.

Creation of Variable Length and Sequence in the Linker Region

A preferred approach is to create a library of two domain polypeptides ($D_1$-L-$D_2$) wherein each library member varies from all others in L. In other words, randomness between the domains is found in the linkers that link them. This permits the generation of an array of $D_1$-L-$D_2$ products, particularly in a plant expression system, from which one can select one, or an array, of optimally folded, optimally functioning products.

In this approach, two cloned domains are amplified and a linker of variable length and variable sequence is introduced between them using an amplification method such as PCR.

To achieve this, a portion of the 3' end of the downstream primer for the upstream domain and the 3' end of the upstream primer for the downstream domain are complementary to the respective domain sequence being amplified. ("Downstream" and "upstream" are relative to the linker). However, a portion of the 5' end of the downstream primer for the upstream domain and/or the 5' end of the upstream primer for the downstream domain are not complementary to the respective domain being amplified. This noncomplementary segment of the primers, termed a "nontemplated sequence," contains a repeated pattern of degenerate triplet bases which, at the nucleic acid level, join the upstream to the downstream domain.

The upstream and downstream primers for amplifying $D_1$ and $D_2$ are mixed with a DNA polymerase and other necessary reactants for amplification. See Innis et al., supra, for details. The reaction mixture is subjected to multiple temperature cycles to melt DNA duplexes, allow annealing of primers to template and polymerization of the PCR product. During the first cycle the DNA polymerase carries out "first strand" synthesis until the temperature is raised sufficiently to melt the duplexes. Thereafter, when the temperature is lowered to the annealing temperature, the primers will anneal to the first strand DNA. The DNA polymerase will then make a "second strand" as the polymerization temperature of the cycle is reached. This results in exponential accumulation of the domain being amplified. Because of the nontemplated sequences, the amplified domain-encoding DNA will form a population (library) of molecules with a repeated pattern of degenerate bases at the 3' end of the upstream product and the 5' end of the downstream product.

Due to the nature of the repeated pattern of degenerate triplet bases in the nontemplated sequences of the amplification pairs, the PCR products are diverse in sequence and length in the L region. The length diversity is mostly likely due to duplex formation of the L region of the primers with bubbles or loops in the middle due to base pair mismatching. The 3'-5' exonuclease and the 5'-3' polymerase activities serve to delete or extend the length of the primer sequence.

To shorten the L sequence, a primer containing the repeated triplet is annealed to a complementary strand that has already incorporated the L sequence. The degenerate primer can then anneal to form a duplex with a bubble at the site of unpaired bases, and leave an unpaired 3' extension (overhang), as diagrammed below (underscored).

Duplex with Bubble and 3' Overhang

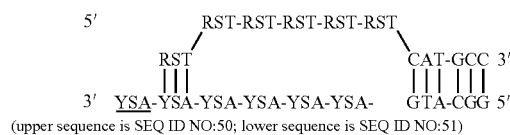
(upper sequence is SEQ ID NO:50; lower sequence is SEQ ID NO:51)

An enzyme such as PFU or Vent that has 3'-5' exonuclease activity will degrade the 3' extension in the 5' direction of the complementary strand until it reaches the annealed portion of the duplex. In this manner one or more triplet repeats can be removed from the PCR product, thereby shortening the peptide linker L by one (or more) amino acids.

For extension of the linker L, the "top" strand can anneal to the complementary strand so that a duplex with a 5' extension is formed, as follows:

Duplex with Bubble and 5' Overhand.

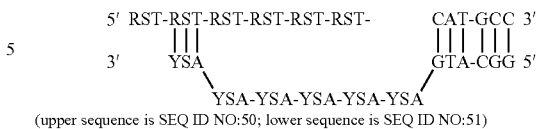
(upper sequence is SEQ ID NO:50; lower sequence is SEQ ID NO:51)

The polymerase present in the amplification reaction, e.g., Taq polymerase, can extend the PCR product by one or more triplet repeat codons. Because of its 5'-3' polymerase activity, the enzyme can fill in the 5, extension, thereby lengthening the linker region by one or more repeated triplets. This will extend of the peptide linker by one or more amino acids. If the polymerase in the PCR lacks 3'-5' exonuclease activity, and if no enzyme with 3'-5' exonuclease activity is present, then only extensions of triplet nucleotides should occur.

To promote bubble formation, the 5' end of at least one primer must contain the same degenerate bases in at least two terminal codons to prevent slippage. That is, there must be two triplet repeats with the same sequence (e.g., 5' rst-rst3', or 5' ysa-ysa3', etc.) at the 5' end of at least one of the primers used to amplify a domain.

To retain the proper reading frame, which is important if the fused nucleic acid is to express a protein (as is the case with an scFv), several rules should be observed in designing the degeneracy of the nontemplated region of the primers that will be the L region. The degenerate triplet repeats should obey one of the following rules:

(a) position 1 of the triplet cannot contain the same base as position 2; or (b) position 2 of the triplet cannot contain the same base as position 3; or (c) position 1 of the triplet cannot contain the same base as position 3.

For example, a repeated triplet rst and ysa will obey these rules. The following combinations of bases fulfill those rules: rst=agt, act, ggt, gct and ysa=tca, tga, cca, cga. Other degenerate sequences can also fulfill these rules. For example str (which can be gta, gtg, cta, or ctg) or ayr (which can be aca, acg, ata or atg) could serve as a repeated triplet.

Another degenerate triplet sequence useful in this invention is nvt which can be any of 12 different codons encoding 11 different amino acids. The degenerate triplet nws can be any of 16 different codons encoding 12 different amino acids. The degenerate triplet csy does not adhere to these rules because it could be ccc (which does not comply). Similarly, any other degenerate sequence that can be a triplet of identical bases (i.e., ccc, aaa, ggg, or ttt) would not obey these rules and would thus be excluded as a repeated triplet.

Restriction enzyme recognition sequences can be incorporated into the primers to facilitate cloning and orientation of, for example the IgV region domains (or any other polypeptide domains) with respect to each other. For example, a restriction endonuclease site may be incorporated in the 5' end of the upstream amplification primer for the $D_1$ domain, which will facilitate ligation of the 5' end of the upstream domain to the 5' end of a restricted vector into which that fragment is being subcloned. Likewise the same or a different restriction site can be incorporated in the 5' end of the downstream amplification primer for the downstream domain. The resulting PCR product can then be restricted with the respective endonuclease(s) for subsequent ligation into a vector that has complementary sequence(s) to the PCR products. Alternatively the same restriction site can be used, and the subclones can be screened by DNA sequencing, PCR, restriction enzyme digestion, etc., to determine if the correct orientation has been achieved.

Ligation of the PCR Products

The 3' end of the upstream PCR product and the 5' end of the downstream PCR product can be ligated to one another (*Methods in Enzymology: Guide to Molecular Cloning Techniques*, Berger et al., eds, 1987)). If both ends of these products are blunt, the 5' phosphates can be phosphorylated by T4 polynucleotide kinase and the reaction products ligated with T4 DNA ligase. If the ends of the PCR products are complementary or can be made complementary through restriction endonuclease digestion, then a sticky end ligation can be performed wherein the complementary ends are ligated with T4 DNA ligase. Likewise the 5' end of the upstream PCR product and/or the 3' end of the downstream PCR product can be ligated to a restricted vector in a blunt end or a sticky end ligation.

To increase the sequence and length complexity of the linker region of the population of dual-domain molecules, such as an scFv, multiple PCR reaction products of $D_1$ and $D_2$ can be combined. For example, a PCR reaction of $D_1$ and/or $D_2$ where the degenerate triplet is repeated six times can be combined with PCR reactions of the $D_1$ and/or $D_2$ where the degenerate triplet is repeated nine times and ligated into the appropriate vector. The combination of the PCR products will increase the length and sequence complexity observed in the L region.

The complexity of the linker sequences obtained in the population or "library" can be pre-determined by the number of different amino acids designed into the nontemplate sequence of the PCR amplification primers used to amplify the domains. The number of amino acids encoded by the nontemplated sequence is determined by the nucleotide degeneracy designed into each codon triplet.

In one example, the desired complexity of the linker sequence present in a library is limited to two amino acids, Ala and Gly. The nontemplated sequence preferred for this linker combination would be repeats of the codon triplet gst (=gct and ggt), where gct encodes Ala' and ggt encodes Gly.

In a second example, the desired complexity of the linker sequence present in a library is increased to six amino acids, Ala, Gly, Ser, Thr, Lys and Asp. The nontemplated sequence preferred for this linker combination would be repeats of the codon triplet rvt (=gct, ggt, agt, act, aat and gat), wherein the following amino acids are encoded:

| gct Ala | ggt-Gly | aat-Lys |
| agt-Ser | act-Thr | gat-Asp |

The same approaches are used to generate multi-domain polypeptides of higher order, e.g., three- or four-domain polypeptides. These can comprise all different domains or one or more domains can be repeated. General structures for such molecules is as follows (where D is a polypeptide domain and L is a linker):

| $D_1$-$L_1$-$D_1$ | $D_1$-$L_1$-$D_2$ |
| $D_1$-$L_1$-$D_2$-$L_2$-$D_2$ | $D_1$-$L_1$-$D_2$-$L_2$-$D_3$ |
| $D_1$-$L_1$-$D_2$-$L_2$-$D_3$-$L_3$-$D_4$ | etc. |

The different linkers between the various domains can vary in complexity. This will depend on the structural relationship required for the proper function of each domain for its intended purpose. Thus, in the example of an scFv molecule with a single idiotype or with a single ligand-binding specificity, the two domains must function in concert for proper binding. In a 3-domain polypeptide which is an scFv of desired binding specificity wherein the third domain $D_3$ is a toxin, there are fewer constraints on the "interaction" between the toxin domain and either of the two binding domains. In that case, the linker $L_2$ between one of the scFv domains and the toxin domain can be different, less complex than the linker $L_1$ between the two domains ($D_1$ and $D_2$) that comprise the scFv polypeptide.

In a library of multi-domain polypeptides, not every pair of domains is necessarily be joined by a linker according to the present invention. Thus, two or more adjacent domains may be (1) linked directly as may occur in their native state (if they are derived from naturally dual- or multi-domain proteins), or (2) linked by a "conventional" linker well-known in the art. In yet another embodiment, a particular linker identified using the present invention and derived as a member of a random linker library may be a preferred choice for use as a non-random linker between two given domains in a multi-domain polypeptide. These various embodiments can be depicted in the following (non-limiting) manner:

$D_1$-$L_1$-$D_2$-$D_3$
$D_1$-$L_1$-$D_2$-$D_3$-$D_4$
$D_1$-$L_1$-$D_2$-$D_3$-$D_4$-$D_5$
$D_1$-$L_1$-$D_2$-$D_3$-$D_4$-$L_2$-$D_5$
etc.

In the four formulas shown above, $L_1$ and $L_2$ indicate random linker members of the libraries of the present invention. All other domains shown bonded to adjacent domains without a linking L may be (1) directly bonded to one another as described above; (2) linked by a conventional linker known in the art; or (3) linked by a fixed linker discovered in a random linker library according to this invention but inserted as a predetermined, non-random, non-varying linker in the particular location. As noted in the Summary section, above a multi-domain polypeptide herein may be composed of up to about 20 domains. For example, a 10-domain polypeptide may have anywhere between 1 and 9 linkers L according to this invention. If a 10 domain polypeptide has on one such linker $L_1$ linking two domains, the other 8 domains are either directly bonded to one another or linked by conventional or other predetermined linker groups.

Expression System for Production of the Dual-domain Polypeptide

A number of well-known heterologous expression systems in bacterial, insect, mammalian and plant were discussed above, each with its advantages and disadvantages. The present invention is particularly suited for plant expression.

A number of transformation methods permit expression of heterologous proteins in plants. Some involve the construction of a transgenic plant by integrating DNA sequences encoding the protein of interest into the plant genome. The time it takes to obtain transgenic plants may be too long for the rapid production certain embodiments such as a tumor vaccine polypeptide. An attractive solution (an alternative to such stable transformation) is transient transfection of plants with expression vectors. Both viral and non-viral vectors capable of such transient expression are available (Kumagai, M. H. et al. (1993) *Proc. Nat. Acad. Sci. USA* 90:427-430; Shivprasad, S. et al. (1999) *Virology* 255:312-323; Turpen, T. H. et al. (1995) *BioTechnology* 13:53-57; Pietrzak, M. et al. (1986) *Nucleic Acid Re.* 14:5857-5868; Hooykaas, P. J. J. and Schilperoort, R. A. (1992) *Plant Mol. Biol.* 19:15-38), although viral vectors are easier to introduce into host cells, spread by infection to amplify the expression and are therefore preferred.

Chimeric genes, vectors and recombinant viral nucleic acids of this invention are constructed using conventional techniques of molecular biology. A viral vector that expresses heterologous proteins in plants preferably includes (1) a native viral subgenomic promoter (Dawson, W. O. et al. (1988) *Phytopathology* 78:783-789 and French, R. et al. (1986) *Science* 231:1294-1297), (2) preferably, one or more non-native viral subgenomic promoters (Donson, J. et al. (1991) *Proc. Nat. Acad. Sci. USA* 88:7204-7208 and Kumagai, M. H. et al. (1993) *Proc. Nat. Acad. Sci. USA* 90:427-430), (3) a sequence encoding viral coat protein (native or not), and (4) nucleic acid encoding the desired heterologous protein. Vectors that include only non-native subgenomic promoters may also be used. The minimal requirement for the present vector is the combination of a replicase gene and the coding sequence that is to be expressed, driven by a native or non-native subgenomic promoter. The viral replicase is expressed from the viral genome and is required to replicate extrachromosomally. The subgenomic promoters allow the expression of the foreign or heterologous coding sequence and any other useful genes such as those encoding viral proteins that facilitate viral replication, proteins required for movement, capsid proteins, etc. The viral vectors are encapsidated by the encoded viral coat proteins, yielding a recombinant plant virus. This recombinant virus is used to infect appropriate host plants. The recombinant viral nucleic acid can thus replicate, spread systemically in the host plant and direct RNA and protein synthesis to yield the desired heterologous protein in the plant. In addition, the recombinant vector maintains the non-viral heterologous coding sequence and control elements for periods sufficient for desired expression of this coding sequence.

The recombinant viral nucleic acid is prepared from the nucleic acid of any suitable plant virus, though members of the tobamovirus family are preferred. The native viral nucleotide sequences may be modified by known techniques providing that the necessary biological functions of the viral nucleic acid (replication, transcription, etc.) are preserved. As noted, one or more subgenomic promoters may be inserted. These are capable of regulating expression of the adjacent heterologous coding sequences in infected or transfected plant host. Native viral coat protein may be encoded by this RNA, or this coat protein sequence may be deleted and replaced by a sequence encoding a coat protein of a different plant virus ("non-native" or "foreign viral"). A foreign viral coat protein gene may be placed under the control of either a native or a non-native subgenomic promoter. The foreign viral coat protein should be capable of encapsidating the recombinant viral nucleic acid to produce functional, infectious virions. In a preferred embodiment, the coat protein is foreign viral coat protein encoded by a nucleic acid sequence that is placed adjacent to either a native viral promoter or a non-native subgenomic promoter. Preferably, the nucleic acid encoding the heterologous protein, e.g., an immunogenic polypeptide to be expressed in the plant, is placed under the control of a native subgenomic promoter.

An important element of this invention, that is responsible in part for the proper folding and copious production of the heterologous protein (exemplified as the immunogenic scFv polypeptide), is the presence of a signal peptide sequence that directs the newly synthesized protein to the plant secretory pathway. The sequence encoding the signal peptide is fused in frame with the DNA encoding the polypeptide to be expressed. A preferred signal peptide is the α-amylase signal peptide.

In another embodiment, a sequence encoding a movement protein is also incorporated into the viral vector because movement proteins promote rapid cell-to-cell movement of the virus in the plant, facilitating systemic infection of the entire plant.

Either RNA or DNA plant viruses are suitable for use as expression vectors. The DNA or RNA may be single- or double-stranded. Single-stranded RNA viruses preferably may have a plus strand, though a minus strand RNA virus is also intended.

The recombinant viral nucleic acid is prepared by cloning in an appropriate production cell. Conventional cloning techniques (for both DNA and RNA) are well known. For example, with a DNA virus, an origin of replication compatible with the production cell may be spliced to the viral DNA.

With an RNA virus, a full-length DNA copy of the viral genome is first prepared by conventional procedures: for example, the viral RNA is reverse transcribed to form +subgenomic pieces of DNA which are rendered double-stranded using DNA polymerases. The DNA is cloned into an appropriate vector and inserted into a production cell. The DNA pieces are mapped and combined in proper sequence to produce a full-length DNA copy of the viral genome. Subgenomic promoter sequences (DNA) with or without a coat protein gene, are inserted into nonessential sites of the viral nucleic acid as described herein. Non-essential sites are those that do not affect the biological properties of the viral nucleic acid or the assembled plant virion. cDNA complementary to the viral RNA is placed under control of a suitable promoter so that (recombinant) viral RNA is produced in the production cell. If the RNA must be capped for infectivity, this is done by conventional techniques.

Examples of suitable promoters include the lac, lacuv5, trp, tac, ip1 and ompF promoters. A preferred promoter is the phage SP6 promoter or $T_7$ RNA polymerase promoter.

Production cells can be prokaryotic or eukaryotic and include *Escherichia coli*, yeast, plant and mammalian cells.

Numerous plant viral vectors are available and well known in the art (Grierson, D. et al. (1984) *Plant Molecular Biology*, Blackie, London, pp. 126-146; Gluzman, Y. et al. (1988) *Communications in Molecular Biology: Viral Vectors*, Cold Spring Harbor Laboratory, New York, pp. 172-189). The viral vector and its control elements must obviously be compatible with the plant host to be infected. Suitable viruses are (a) those from the tobacco mosaic virus (TMV) group, such as TMV, tobacco mild green mosaic virus (TMGMV), cowpea mosaic virus (CMV), alfalfa mosaic virus (AMV), Cucumber green mottle mosaic virus—watermelon strain (CGMMV-W), oat mosaic virus (OMV),
(b) viruses from the brome mosaic virus (BMV) group, such as BMV, broad bean mottle virus and cowpea chlorotic mottle virus,
(c) other viruses such as rice necrosis virus (RNV), geminiviruses such as Tomato Golden Mosaic virus (TGMV), Cassaya Latent virus (CLV) and Maize Streak virus (MSV).

A preferred host is *Nicotiana benthamiana*. The host plant, as the term is used here, may be a whole plant, a plant cell, a leaf, a root shoot, a flower or any other plant part. The plant or plant cell is grown using conventional methods.

A preferred viral vector for use with *N. benthamiana* is expression vector pBSG1250 (pTTOSA derivative) containing a hybrid fusion of TMV and tomato mosaic virus (ToMV) (Kumagai, M H. et al. (1995) *Proc. Natl. Acad. Sci. USA* 92:1679-1683). The inserted subgenomic promoters must be compatible with TMV nucleic acid and capable of directing transcription of properly situated (e.g., adjacent) nucleic acids sequences in the infected plant. The coat protein should permit the virus to systemically infect the plant host. TMV coat protein promotes systemic infection of *N. benthamiana*.

Infection of the plant with the recombinant viral vector is accomplished using a number of conventional techniques known to promote infection. These include, but are not limited to, leaf abrasion, abrasion in solution and high velocity water spray. The viral vector can be delivered by hand, mechanically or by high pressure spray of single leaves.

Purification of the Protein/Polypeptide Product

The dual-domain polypeptide produced in plants is preferably recovered and purified using standard techniques. Suitable methods include homogenizing or grinding the plant or the producing plant parts in liquid nitrogen followed by extraction of protein. If for some reason it is not desirable to homogenize the plant material, the polypeptide can be removed by vacuum infiltration and centrifugation followed by sterile filtration. Protein yield may be estimated by any acceptable technique. Polypeptides are purified according to size, isoelectric point or other physical property. Following isolation of the total secreted proteins from the plant material, further purification steps may be performed. Immunological methods such as immunoprecipitation or, preferably, affinity chromatography, with antibodies specific for epitopes of the desired polypeptide may be used.

To facilitate purification, the viral vector can be engineered so that the protein is produced with an affinity tag that can be exploited at the purification stage. An examples of such a tag is the histidine (H is) tag that permits purification on a metal (e.g., nickel) affinity column. Other affinity tags are well-known in the art and need not be described here.

Various solid supports may be used in the present methods: agarose®, Sephadex®, derivatives of cellulose or other polymers. For example, staphylococcal protein A (or protein L) immobilized to Sepharose® can be used to isolate the target protein by first incubating the protein with specific antibodies in solution and contacting the mixture with the immobilized protein A which binds and retains the antibody-target protein complex.

Using any of the foregoing or other well-known methods, the polypeptide is purified from the plant material to a purity of greater than about 50%, more preferably greater than about 75%, even more preferably greater than about 95%.

Determination of Correct Folding

Critical for certain properties such as immunogenicity is the protein's conformation in solution. The conformation of the relevant epitopes of the dual-domain polypeptide in solution preferably resemble or mimic the same epitopes of the native protein. By producing polypeptides in plants, and targeting them to the plant's secretory pathway, the present invention insures that the polypeptide is secreted in soluble, optimally folded, form.

A preferred reagent to be used in determining proper folding is a specific antibody, preferably a mAb, which (1) binds to an epitope of the polypeptide when the chains are correctly folded but (2) does not bind when the epitopes are denatured. The antibody is employed in any of a number of immunological assays, including dot blot, western blot, immunoprecipitation, radioimmunoassay (RIA), and enzyme immunoassays (EIA) such as an enzyme-linked immunosorbent assays (ELISA). In preferred embodiments, when such antibodies are available, Western blots and ELISAs are employed to verify correct folding of the relevant parts of the dual domain (or multi-domain) polypeptide produced in the plant.

Additional Analysis of the Dual-Domain Molecule

DNA encoding the dual domain polypeptide can be sequenced, yielding a deduced amino acid sequence of its encoded product. If the DNA molecule has been subcloned, it can be excised from the vector with a restriction enzyme and the resulting fragments analyzed on agarose gels to determine the size of the fragments.

If the DNA molecule itself has the binding domains of interest, the subcloned DNA molecule (or excised fragment) can be assayed for binding to the relevant ligand.

If the DNA molecule encodes a dual-domain ribozyme, then the ribozyme RNA can be transcribed from the vector. The coding sequence can be excised with restriction enzymes and contacted with an RNA polymerase (along with ribonucleotides and other required factors) to transcribe the dual-domain RNA. The ribozyme can then be quantified and its enzymatic activity measured in an appropriate assay.

A DNA molecule encoding a dual-domain polypeptide is first expressed. If desired, the DNA can be additionally modified to include sequences that will permit or optimize expression in an appropriate host or in an in vitro transcription/translation system. Once expressed, the polypeptide is then subjected to appropriate functional assays, e.g., measurement of enzymatic activity (of either domain). Also the quantity and physical properties of the dual domain polypeptide can be determined, e.g., by SDS-PAGE. Electrophoretic separation can be followed by direct staining of protein or by Western blotting and probing with an appropriate antibody that recognizes an epitope of either domain. If a domain has binding activity, or other functions as have been described above, this can also be measured by conventional means.

Having now generally described the invention, the same will be more readily understood through reference to the following examples which are provided by way of illustration, and are not intended to be limiting of the present invention, unless specified.

The following examples are provided by way of illustration only and not by way of limitation. Those of skill will readily recognize a variety of noncritical parameters which could be changed or modified to yield essentially similar results.

EXAMPLE 1

Generation of a Self/Tumor Antigen from a Single Patient (CJ) that Includes the Idiotype of CJ B Cell Lymphoma The immunogenic scFv protein designated "CJ" was derived from human lymphoma patient (having the initials CJ) and had as its linker $(Gly_4Ser)_3$ SEQ ID NO: 3. Patient CJ had been treated in an earlier passive immunotherapy trial. The CJ molecule (specifically, its V region epitope or epitopes) is recognized by an anti-Id mAb named 7D11. See, also; McCormick, A A et al., Proc Natl Acad Sci USA (1999) 96:703-708).

In an initial attempt to make a human scFv polypeptide, CJ V region genes were sequenced and cloned into a bacterial expression system using a (Gly$_4$Ser)$_3$ SEQ ID NO: 3 linker. Although targeted to the periplasm with a PEL-b leader, CJ scFv protein was sequestered in insoluble inclusion bodies. When mice were immunized with CJ scFv made in bacteria, no anti-CJ anti-idiotype antibody responses were detected.

Derivatives of CJ were generated by producing linkers having random length and sequence that was part of general PCR based cloning strategy described herein.

Four reactions were carried out. In the first and second, the sequence encoding the V$_H$ domain was amplified from a cDNA clone of the lymphoma cells from patient CJ using the following synthetic oligonucleotides:

V$_H$F: 5' gtg gcatgc agg ttc aac tgg tgg agt ctg (SEQ ID NO:4)
V$_H$R: 5' (asy)$_x$ tga gga gac ggt gac cag ggt tc (SEQ ID NO:5)

The SphI restriction site is underscored. In the first reaction x was 6:
asy asy asy asy asy asy tga gga gac ggt gac cag ggt tc (SEQ ID NO:6)

In the second reaction, x was 9, giving SEQ ID NO:7:
asy asy asy asy asy asy asy asy asy tga gga gac ggt gac cag ggt tc (In general, the number of triplets (x) can be 1 to about 50)

In the third and fourth PCR reactions, the sequence encoding the V$_L$ domain was amplified from a cDNA clone of CJ using the following synthetic oligonucleotides:

V$_L$F: 5' (rst)$_z$ gac att cag atg acc cag tct cct tc (SEQ ID NO:8)
V$_L$R: 5' cac cctagg cta tcg ttt gat cag tac ctt ggt ccc ctg (SEQ ID NO:9)

The AvrII site is underscored. In the third reaction z was 6:
rst rst rst rst rst rst gac att cag atg acc cag tct cct tc (SEQ ID NO:10)

In the fourth reaction, z was 9 (SEQ ID NO:11):
rst rst rst rst rst rst rst rst rst gac att cag atg acc cag tct cct tc (In general, the number of triplets (z) can be 1 to about 50.)

Following amplification, the four PCR products were purified and digested with SphI for the V$_H$ chain PCR product and AvrII for the V$_L$ chain PCR product. The digests were electrophoresed on an agarose gels and the four digested PCR fragments were purified, combined and ligated into a Geneware® expression vector pBSG1250 (pTTOSA derivative) containing a hybrid fusion of TMV and ToMV (Kumagai, et al., supra) that had been digested with the restriction enzymes SphI and AvrII. In the particular Geneware® vector, the SphI site lies downstream of the TMV U1 CP subgenomic promoter and the α amylase signal peptide sequence. The SphI site in the primer VHF is in-frame with the SphI site in the α amylase signal peptide sequence. After ligation of both the $V_H$ and $V_L$ PCR fragments into the Geneware® vector, the DNA was treated with polynucleotide kinase and ATP to incorporate phosphates at the blunt 5' ends of the initial PCR products.

Following the kinase reaction, the DNA was ligated back upon itself, to generate circular plasmids. The ligated DNA was transformed into *E. coli* (using electroporation), and the transformed cells were plated on selective media containing 50 μg/ml ampicillin. Plasmid DNA was purified from individual ampicillin-resistant *E. coli* colonies and transcribed with T7 RNA polymerase to generate infectious transcripts of individual clones.

Transcripts were transfected into *N. tobacum* plant protoplasts using a PEG-based transfection protocol essentially as described in Lindbo et al., *Plant Cell* 5:1749-1759 (1993), and transfected protoplasts were incubated in protoplast culture medium for several days. The latter medium contained 265 mM mannitol, 1× Murashige minimal organics medium (Gibco/BRL), 1.5 mM $KH_2PO_4$, 0.2 μg/ml 2,4-dichlorophenoxyacetic acid, 0.1 μg/ml kinetin, and 5% coconut water (Sigma). Protoplasts were cultured at a density of about $10^6$ cells/ml. Plasmid DNA was purified from at least 10 to 50 individual colonies from each cloning experiment.

Approximately 1-4 days after transfection, protein samples were collected from the individual protoplast samples. Culture medium (200-500 μl) was concentrated about 10-fold by speed vacuum evaporation or Microcon sample concentrator.

Since this cloning strategy included a signal peptide sequence designed to promote secretion of the protein product by the plant cells into the culture medium, medium samples were also analyzed by SDS-PAGE followed by Coomassie blue staining and/or by Western blotting.

The starting scFv incorporated the standard $(Gly_4Ser)_3$ SEQ ID NO: 3 linker sequence; the other scFv chains were randomly selected from the transformants obtained from the linker library cloning experiment that utilized the cloned PCR products generated from the four primers (SEQ ID NO:4-11, above). Culture supernatants from equivalent numbers of cells were electrophoresed (SDS-PAGE), and the gels were transferred to nitrocellulose membranes for Western analysis with mAb 7D11 (see above).

Some selected linker library members that were screened randomly appeared to express and accumulate as much or more CJ protein as did the CJ scFv having the conventional linker $(Gly_4Ser)_3$ SEQ ID NO: 3.

DNA of those library members expressing particularly high amounts of CJ scFv was sequenced. Results are shown in Table 2. Plasmid DNAs for selected clones were prepared and sequenced by standard methods. From the nucleotide sequences of the various CJ derived constructs, the linker sequence of individual clones was deduced. Table 2 lists some of the nucleotide and amino acid linker sequences obtained and indicates "relative expression" which means the amount of expression relative to the same protein but with the $(Gly_4Ser)_3$ SEQ ID NO: 3 linker.

TABLE 2

Analysis of select members of the CJ linker library experiment in plant protoplasts

| Clone | Linker Region Nucleotide Sequence (lower case) and Amino Acid Sequence (upper case) | SEQ ID NO: | Length (aa) | RE* |
|---|---|---|---|---|
| #24 | actactgctactggtgctagtactactgctggtgctagt | 12 | 13 aa | ++ |
| | T T A T G A S T T A G A S | 13 | | |
| #36 | Gctactgctgctagtggtgctgctgctggtggtggtact | 14 | 13 aa | + |
| | A T A A S G A A A G G G T | 15 | | |

TABLE 2-continued Analysis of select members of the CJ linker library experiment in plant protoplasts

| Clone | Linker Region Nucleotide Sequence (lower case) and Amino Acid Sequence (upper case) | SEQ ID NO: | Length (aa) | RE* |
|---|---|---|---|---|
| #37 | Gctactggtgctagtactagtgctactgctggtggtagt<br>A T G A S T S A T A G G S | 16<br>17 | 13 aa | ++ |
| #20 | Agtactgctgctggtactagtagtggtagtagtactggt<br>S T A A G T S S G S S T G | 18<br>19 | 13 aa | ++ |
| #12 | Gctagtactgctactagtagtggtggtggtggtactggtagtagtgctgct<br>A S T A T S S G G G T G S S A A A | 20<br>21 | 17 aa | + |
| #16 | Gctactagtactgctgctgctggtgctactagtgctactggtggtgctagtggtactggt<br>A T S T A A A G A T S A T G G A S G T G | 22<br>23 | 20 aa | +++ |
| #30 | Actggtgctagtggtgctactagtagtggtagtagtagt<br>T G A S G A T S S G S S S | 24<br>25 | 13 aa | +++ |

*RE = Relative Expression to the (Gly₄Ser)₃ SEQ ID NO:3 clone

DNA sequencing revealed that the clones did not have the same nucleotide or amino acid sequences but rather, demonstrated amino acid and nucleotide length diversity. Table 2 shows a sampling of clones with L's ranging from 13 to 20 amino acids. This range was apparently a result of mispriming during PCR amplification of the $V_H$ and $V_L$ coding sequences. Since the linker coding sequences of the oligonucleotides used in this experiment contain stretches of low complexity nucleotide sequences (i.e., $asy_x$ or $rst_z$ and), multiple mispriming events are likely. In conjunction with DNA polymerase/exonuclease activities present during PCR, this could lead to an increase or a decrease in the number of codons comprising the L sequences.

The quantities of CJ scFv protein produced also varied (relative to the CJ scFv with the (Gly₄Ser)₃ SEQ ID NO: 3 linker). This indicates that both the length and the sequence of the linker region affects the amount of protein produced by the plant cells or plants.

EXAMPLE 2

Expression of scFv Product in Whole Plants

The process described in Example 1 is repeated except that whole plants are used along with a suitable expression system for producing the scFv products.

Expressed products are screened by SDS-PAGE/Coomassie blue staining and/or Western blotting. The results indicate a varied amount of scFv product produced. The highest yielding clones are selected for production of the vaccine scFv.

Expression System

The DNA fragments encoding the dual-domain scFv fragments having the V regions of the CJ human lymphoma were generated as in Example 1 and cloned into vector pBSG1250. In this vector, a TMV coat protein subgenomic promoter is located upstream of the insertion site of the CJ sequence. Following infection, this TMV coat protein subgenomic promoter directs initiation of the CJ RNA synthesis in plant cells at the transcription start point ("tsp"). The rice α amylase signal peptide (O'Neill, S D et al. (1990) Mol. Gen. Genet. 221:235-244), fused in-frame to the CJ sequence, encodes a 31 residue polypeptide which targets proteins to the secretory pathway (Firek, S. et al. (1994) Transgenic Res. 3:326-331), and is subsequently cleaved off between the C-terminal Gly of the signal peptide and the N-terminal Met of the expressed CJ scFv protein. The sequence encoding CJ scFv has been introduced between the 30K movement protein and the ToMV coat protein (Tcp) genes. An T7 phage promoter has been introduced upstream of the viral cDNA, allowing for transcription of infective genomic plus-strand RNA.

Capped infectious RNA was made in vitro from 1 µg plasmid, using a T7 message kit from Ambion. Synthesis of the message was quantified by gel electrophoresis and approximately 2 µg of the in vitro transcribed viral RNA was applied with an abrasive to the lower leaves (approximately 1-2 cm in size) of N. benthamiana (Dawson, WO-et al. (1986) Proc. Natl. Acad. Sci. USA 83:1832-1836). Transcription of subgenomic RNA encoding the CJ scFv protein was initiated after infection at the indicated transcription start point. High levels of subgenomic RNA species were synthesized in virus-infected plant cells (Kumagai, M H. et al. (1993) Proc. Natl. Acad. Sci. USA 90:427-430), and serve as templates for the translation and subsequent accumulation of CJ scFv protein.

Characterization of Clones

Signs of infection were visible after 5-6 days as mild leaf deformation, with some variable leaf mottling and growth retardation. Eleven to fourteen days post inoculation, the secreted proteins were isolated. Leaf and stem material was harvested, weighed and then subjected to a 700 mm Hg vacuum for 2 min in infiltration buffer (100 mM Tris HCl, pH 7.5 and 2 mM EDTA). Secreted proteins (hereafter termed "interstitial fraction" or "IF") were recovered from infiltrated leaves by mild centrifugation at 2000 g (Beckman JA-14) on supported nylon mesh discs, concentrated approximately 10-fold in Centricon-10 (Amicon) concentrators. Total protein was measured by the Bradford method (Bradford, M. (1976) Anal. Biochem. 72:248-254) and stored at −80° C. until used.

The secreted material was analyzed for the presence of soluble CJ scFv protein by the SDS-PAGE followed by Western blot with CJ mAb 7D11. About 3 µg of IF protein were separated by SDS-PAGE and transferred to nitrocellulose membrane in standard Tris-glycine buffer with 20% methanol at 150V for 1 hour. After transfer, blots were treated for 20 minutes at room temperature with blocking buffer (50 mM Tris pH 8, 150 mM NaCl, 1 mM EDTA, 2.5% non-fat dry milk, 2.5% BSA and 0.05% Tween 20) followed by a 16 hr incubation at 4° C. in blocking buffer plus 1 µg/ml purified 7D11 antibody. After three 15 minute washes (100 mM Tris pH 8, 150 mM NaCl, 1 mM EDTA and 0.1% Tween 20), membranes were incubated for 1 hour in blocking buffer plus 1 µg/ml goat anti-mouse IgG-HRP (Southern Biotechnology). After three 15 minute washes, Western blots were developed by Enhanced Chemiluminescence (ECL) (Amersham) according to manufacturers instructions. Exposure times ranged from 1 to 5 seconds. No cross reactivity to plant proteins was observed (testing IF extracts from control infected plants).

Individual clones were sequenced, analyzed for reading frame and amino acid identity to the original CJ Ig sequence and then screened for protein expression in infected plants. FIG. 1 shows the results of 9 individual CJ scFv expressing clones that demonstrated various levels of protein accumulation. Clones 20 and 30 showed high levels of expression, as well as accumulation of protein dimmers. Clone C contained a modification of the $(Gly_4Ser)_3$ SEQ ID NO: 3 linker.

From the sequence data, the linker sequences for individual clones were deduced. The clone numbers in Table 3 are the same as those listed in Table 2. As above, relative expression relates to the scFv protein having the $(Gly_4Ser)_3$ SEQ ID NO: 3 linker.

As above, differences were observed in the expression of various CJ scFv-based clones in whole plants. Interestingly, some clones that were expressed in plant protoplasts were not expressed in whole plants. For example, clone #16 which was strongly expressed in plant protoplasts was apparently not expressed in whole plants. Nevertheless, the methods disclosed for generating the linker regions with varying length and sequence permit the screening of large numbers of clones for their expression in either plant protoplast or whole plants.

The quality of CJ protein, optimized by the random linker library, was validated by two methods. First, CJ protein was purified by affinity chromatography using immobilized 7D11 anti-idiotype mAb. This method requires that the CJ protein bind to the anti-Id column under physiological conditions. Such binding will not occur if the protein is not folded correctly. Protein was bound under normal pH and was eluted by 50 mM diethylamine pH 11.5, then immediately dialyzed against normal saline. Material was quantitated by ELISA using 7D11 and using standard protein determination.

The second, more stringent, assay for the quality of the CJ protein was a functional assay in animals. Clone CJLL20 (for Linker Library pick #20) was purified by 7D11 affinity chromatography, administered to five mice in 3 bi-weekly immunizations of 30 μg each. Ten days after the third injection, serum was sampled. Using the native idiotype (1D12), or an isotype-matched irrelevant human antibody in a sandwich ELISA, the sera were tested for specific responses to the CJ idiotype. Results are shown in FIG. 2.

Non-specifically antibody responses to xenogeneic human Ig determinants were present in only 3 of the 5 animals and in very low amounts (detected as minimal cross-reactivity of the murine sera to an unrelated human antibody).

The sera of all 5 mice had high titers of anti-CJ antibodies (FIG. 2). Thus, the immune response induced by the dual-domain scFv polypeptide was highly specific for the original $V_H$ and $V_L$ domains of the original Ig, as predicted and as desired. These results suggested that the protein produced in plants was folded correctly so that it could induce an appropriate immune response when administered to subjects.

EXAMPLE 3

Expression of scFv Product in Whole Plants

The process described in Example 2 was repeated except that a different human scFv with unknown expression characteristics was used along with a suitable expression system for producing the scFv products.

TABLE 3

Analysis of select members of the CJ linker library experiment in whole plants

| Clone | Linker Region Nucleotide Sequence (lower case) and Amino Acid Sequence (upper case) | SEQ ID NO: | Length | RE* |
|---|---|---|---|---|
| #24 | actactgctactggtgctagtactactgctggtgctagt | 12 | 13 aa | ++ |
| | T T A T G A S T T A G A S | 13 | | |
| #36 | gctactgctgctagtggtgctgctgctggtggtggtact | 14 | 13 aa | + |
| | A T A A S G A A A G G G T | 15 | | |
| #37 | gctactggtgctagtactagtgctactgctggtggtagt | 16 | 13 aa | ++ |
| | A T G A S T S A T A G G S | 17 | | |
| #20 | Agtactgctgctggtactagtagtggtagtagtactggt | 18 | 13 aa | ++ |
| | S T A A G T S S G S S T G | 19 | | |
| #12 | Gctagtactgctactagtagtggtggtggtggtactggtagtagtgctgct | 20 | 17 aa | + |
| | A S T A T S S G G G G T G S S A A A | 21 | | |
| #30 | Actggtgctagtggtgctactagtagtggtagtagtagt | 24 | 13 aa | +++ |
| | T G A S G A T S S G S S S | 25 | | |

*RE = Relative Expression to the $(Gly_4Ser)_3$ SEQ ID NO:3 clone

Expressed products were screened by SDS-PAGE/Coomassie blue staining. The results indicated that the amount of scFv product produced varied based on linker composition. The highest yielding clones are selected for production of a vaccine scFv.

Expression System

The DNA fragments encoding the dual-domain scFv fragments having the V regions of the Go19 human lymphoma were generated as in Example 1 and cloned into p1324-MBP, a modified 30B vector (Shivprasad, S. et al. (1999) *Virology* 255:312-323), containing a hybrid fusion of TMV and TMGMV-U5 as well as the rice α amylase signal peptide with Sph I and Avr II insert cloning sites.

In this vector, a TMV coat protein subgenomic promoter is located upstream of the insertion site of the Go1 9 sequence. Following infection, this TMV coat protein subgenomic promoter directs initiation of Go19 RNA synthesis in plant cells at the transcription start point ("tsp"). The rice α amylase signal peptide (O'Neill, S D et al. (1990) *Mol. Gen. Genet.* 221:235-244), fused in-frame to the Go19 sequence, encodes a 31 residue polypeptide which targets proteins to the secretory pathway (Firek, S. et al. (1994) *Transgenic Res.* 3:326-331), and is subsequently cleaved off between the C-terminal Gly of the signal peptide and the N-terminal Met of the expressed Go19 scFv protein. The sequence encoding Go19 scFv was been introduced between the 30K movement protein and the TMGMV-U5 coat protein (Tcp) genes. A T7 phage RNA polymerase promoter was introduced upstream of the viral cDNA, allowing for transcription of infective genomic plus-strand RNA.

The Go19 V regions were amplified in four separate PCR reactions. In the first and second reactions, the sequence encoding the $V_H$ domain was amplified from a cDNA clone derived from the lymphoma cells of patient Go19 using the following synthetic oligonucleotides:

$V_H$F: 5' cct gcatgc tgg agg tgc agt tgg tgg aat c (SEQ ID NO:26

$V_H$R: 5' (asy)$_x$ aga gga gac ggt gac cat ga (SEQ ID NO:27)

The SphI restriction site is underscored above. In the first reaction x was 4:

5'-asy asy asy asy aga gga gac ggt gac cat ga (SEQ ID NO:28)

In the second reaction, x was 9 (SEQ ID NO:29):

5'-asy asy asy asy asy asy asy asy asy aga gga gac ggt gac cat ga (In general, the number of triplets (x) can be 1 to about 50)

In the third and fourth PCR reactions, the sequence encoding the $V_L$ domain was amplified from a cDNA clone of Go19 using the following synthetic oligonucleotides:

$V_L$F: 5' (rst) cag tct gcc ctg act cag t (SEQ ID NO:30)

$V_L$R: 5' cac cctagg tca acc aag gac ggt cag gtt ggt c (SEQ ID NO:31)

The Avr II restriction site is underscored above. In the first reaction, z was 6:

5'-rst rst rst rst rst rst cag tct gcc ctg act cag t (SEQ ID NO:32)

In the second reaction, z was 9, giving SEQ ID NO:33:

5'-rst rst rst rst rst rst rst rst rst cag tct gcc ctg act cag t (In general, the number of triplets (z) can be 1 to about 50)

Prior to PCR amplification, the $V_H$R and $V_L$R oligonucleotides were treated with polynucleotide kinase and ATP to add phosphates at the 5' end of the oligonucleotides. Following amplification, the four PCR products are purified and the $V_H$ and $V_L$ products are ligated together to create the scFv. The scFv ligation products are re-purified, restriction digested with SphI and Avr II and the digested scFv is gel isolated and ligated into the Geneware® vector. The ligated DNA was transformed into *E. coli* (using electroporation), and the transformed cells were plated on selective media containing 50 g/ml ampicillin. Plasmid DNA was purified from individual ampicillin-resistant *E. coli* colonies.

Capped infectious RNA was made in vitro from approximately 0.5 µg plasmid, using an T7 message kit from Ambion. Synthesis of the message was evaluated by gel electrophoresis, and approximately 2 µg of the in vitro transcribed viral RNA was encapsidated with purified TMV-U1 coat protein in 100 mM sodium phosphate, pH 7.0 at room temperature for a minimum of 6 hours. Encapsidated transcripts are applied with an abrasive to the lower leaves (approximately 1-2 cm in size) of *N. benthamiana* (W. O. Dawson et al. (1986) *Proc. Natl. Acad. Sci. USA* 83:1832-1836). Transcription of subgenomic RNA encoding the Go19 scFv protein was initiated after infection at the indicated transcription start point. High levels of subgenomic RNA species were synthesized in virus-infected plant cells (M. H. Kumagai et al. (1993) *Proc. Natl. Acad. Sci. USA* 90:427-430), and serve as templates for the translation and subsequent accumulation of Go19 scFv protein.

Characterization of Clones

Signs of infection were visible after 5-6 days as mild leaf deformation, with some variable leaf mottling and growth retardation. Eleven to fourteen days post inoculation, the secreted proteins were isolated. Approximately 0.1 g of infected leaf material was harvested, placed into 96-well glass fiber filtration block (Whatman/Polyfiltronics), submerged in infiltration buffer (20 mM Tris HCl, pH 7.0, 10 mM 2-mercaptoethanol). The tissue is subjected to a 700 mm Hg vacuum for 30 seconds, the vacuum released and the vacuum process is repeated at least one addition round. Residual buffer is removed by a low speed spin at 30×g in a plate centrifuge. Secreted proteins (hereafter termed "interstitial fraction" or "IF") were recovered from infiltrated leaves by mild centrifugation at 1700×g in a plate centrifuge and collected into a 96 well polypropylene plate.

Figure 3:
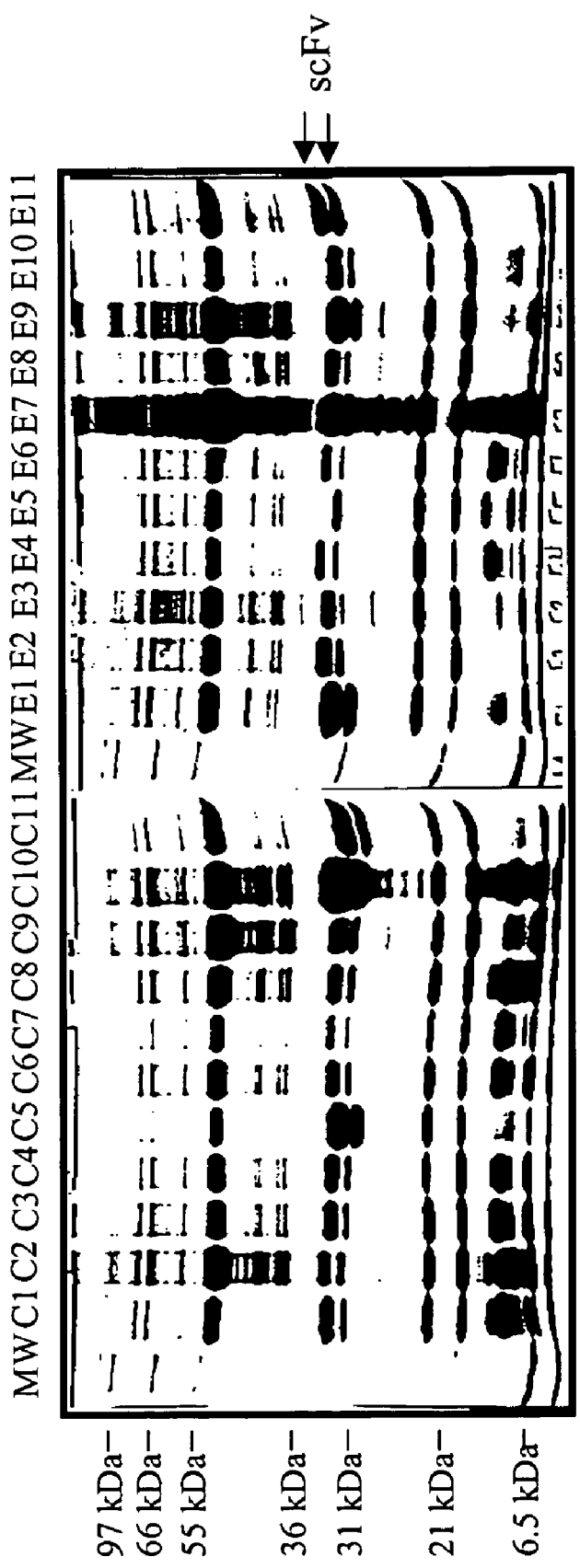
FIG. 3 shows Coomassie stained SDS-PAGE analysis of scFv proteins generated in Example 3 in whole plants. The number of the lane refers to the # of the clone and the arrow indicates the scFv protein. The size in kDa is shown on the left.

The secreted material was analyzed for the presence of soluble Go19 scFv protein by SDS-PAGE. IF (27 µl containing approximately 5 µg of protein) was separated by SDS-PAGE. Linkers from individual clones were sequenced, analyzed for reading frame and amino acid content and then screened for protein expression in infected plants. FIG. 3 shows the results of 22 individual Go19 scFv expressing clones that demonstrated various levels of protein accumulation. Clones C5 and E1 and E9 showed high levels of expression with minimal protease degradation.

From the sequence data, the linker sequences for individual clones were deduced as shown in Table 4.

TABLE 4

Analysis of select members of the Go19 linker library experiment in whole plants

| Clone | Linker Region Nucleotide Sequence (lower case) and Amino Acid Sequence (upper case) | SEQ ID NO: | Length (aa) | RE* |
|---|---|---|---|---|
| #C5 | Ggtgctggtggtggt<br>G  A  G  G  G | 34<br>35 | 5 | *** |
| #C10 | Actggtggtggtggtggtagtggtggtggt<br>T  G  G  G  G  S  G  G  G | 36<br>37 | 10 | *** |
| #C11 | Actactactactgctactactgctggtagtggtgct<br>T  T  T  T  A  T  T  A  G  S  G  A | 38<br>39 | 12 | ** |
| #E1 | Gctagtactggtgct<br>A  S  T  G  A | 40<br>41 | 5 | *** |
| #E9 | Agtactggtagtagtggtgctggt<br>S  T  G  S  S  G  A  G | 42<br>43 | 8 | *** |
| #E3 | Gctagtagtggtgctagtgct<br>A  S  S  G  A  S  A | 44<br>45 | 7 | * |
| #C4 | Gctagtggtggtactgctggtactggtggtagtagtact<br>A  S  G  G  T  A  G  T  G  G  S  S  T | 46<br>47 | 13 | ** |
| #E4 | Actagtggtagtggtgctagtgctgctgctggtggtgctgctgctagtgct<br>T  S  G  S  G  A  S  A  A  A  G  G  A  A  A  S  A | 48<br>49 | 17 | * |

*RE = Relative Expression to Go19 scFv library clones

As above, differences were observed in the expression of various Go19 scFv-based clones in whole plants as well as the degree of degradation indicated by the presence of protein accumulation between the 6.5 kDa and 21 kDa marker bands. The methods disclosed for generating the linker regions with varying length and sequence permit the screening of large numbers of clones for their expression in either plant protoplast or whole plants.

EXAMPLE 4 scFv-Detectably Labeled Conjugates

A mAb to HER-2/neu inhibits growth of cells of the breast cancer cell line SK-Br-3 (ATCC HTB 30) in 6 day culture. Such treatment sensitizes these cells to chemotherapeutic agents (U.S. Pat. No. 5,677,171).

The process of Example 1 is repeated using a $V_H$ and $V_L$ regions of an scFv that specifically binds the HER-2/neu (erbB-2) protein. The scFv gene encoding such a polypeptide is described in Wels et al., *Biotechnology* 10:1128-1132 (1992). Using the same repeated triplet nucleotide sequences as in Example 1, the 3' end of the erbB-2 scFv DNA construct is linked to the 5' end of the horseradish *peroxidase* gene using appropriate PCR primers modeling the method in Example 1.

High yielding clones are identified by measuring for peroxidase activity in the supernatant. High affinity and avidity are determined by immunohistochemical detection, with substrate and chromophore on control samples of a breast cancer cell line that overexpresses HER-2/neu. Comparisons are made to conventional labeled mAbs to HER-2/neu (such as DAKO HercepTest, Dako Corp., Carpinteria, Calif.) to determine which clones produce acceptable scFv proteins.

EXAMPLE 5 scFv-Toxin Conjugate Production

The process of Example 4 is repeated, with the following modification. The gene for the ricin A chain is linked to the 3' end of the scFv DNA construct through the linker region of this invention (made up of repeated triplet nucleotides).

The plant cell clones are grown in 24 well plates and screened initially by measuring secreted protein (PAGE followed by Coomassie blue staining). Two day culture supernatants from the wells in which each clone is growing are tested for cytotoxic activity toward target cells by incubation with active cultures of SK-Br-3 in six well plates (Costar). Cytotoxicity against these targets is determined 48 hours later by microscopic inspection.

High producing clones that generate strong cytotoxicity are selected. Calluses are formed from these cultures to regenerate plants for field growth and large scale production.

Humanized mAb to HER-2/neu is an FDA approved therapeutic for breast cancer (HERCEPTIN, Genentech, Inc., South San Francisco, Calif.). It is expected that toxin-conjugated scFv specific for the same antigen will be at least equally and probably more cytotoxic to human breast cancer cells.

EXAMPLE 6

Production of Dual-Domain Ribozymes

The process of Example 1 is repeated except that DNA encoding two different ribozyme domains is used. The vector that contains the subcloned dual ribozyme domains is transcribed to produce RNA with the properties of the respective ribozyme domains.

The amount of transcribed RNA product can be determined by hybridization with an oligonucleotide probe, by spectrophotometric measurements, etc. The amount of activity of either ribozyme domain can be measured using the appropriate assay.

EXAMPLE 6

Production of Dual DNA Domains

The process of Example 1 is repeated except that two different DNA are used, each of which binds a protein. The plasmid DNA can be produced in large amounts, and the dual DNA domain molecule can be excised with a restriction endonuclease. The resulting fragment has the two linked DNA domains and can be assayed for its ability to bind to a DNA binding protein (e.g., transcription factor, restriction endonuclease, polymerase, etc.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

What is claimed is:

1. A library of linker nucleic acid molecules or sequences, each of which joins two nucleic acid domains or two nucleic acid sequences encoding two polypeptide domains, each of which has a pattern of degenerate repeated triplet nucleotides with the following properties:
   (i) position 1 of each repeated triplet cannot be the same nucleotide as position 2 of the repeated triplet; or
   (ii) position 2 of each repeated triplet cannot be the same nucleotide as position 3 of the repeated triplet; or
   (iii) position 1 of each repeated triplet cannot be the same nucleotide as position 3 of the repeated triplet; and
   (iv) wherein each of said molecules or sequences that joins said domains does not encode $Gly_4Ser$ (SEQ ID NO:52) or a repeat thereof.

2. A method for making the library of linker nucleic acid molecules or sequences of claim 1, comprising:
   (a) obtaining two template DNA sequences that comprise the first and the second domains;
   (b) preparing amplification primer pairs which amplify the first and second domains where each primer pair comprises an upstream primer and a downstream primer, each primer having a 5' end and a 3' end, wherein the downstream primer for the first domain or the upstream primer for the second domain comprises a nontemplated sequence,
   said nontemplated sequence comprising said repeated pattern of degenerate repeated triplet nucleotides, wherein at least two of the 5' terminal triplets of said repeated pattern of degenerate repeated triplet nucleotides have the same degenerate sequence;
   (c) amplifying the domains with the amplification primers to generate at least one population of nucleic acid domains having different lengths and sequences in the nontemplated sequence;
   (d) ligating the nucleic acid domains generated in step (c) to generate said population of dual-domain molecules; and
   (e) excising or amplifying said linker nucleic acid molecules or sequences from said population of dual domain molecules.

* * * * *